United States Patent
Hiller et al.

(10) Patent No.: US 12,195,712 B2
(45) Date of Patent: *Jan. 14, 2025

(54) LINKED PERFUSION TO CONTINUOUS-FLOW STIRRED-TANK REACTOR CELL CULTURE SYSTEM

(71) Applicant: Boehringer Ingelheim International GmbH, Ingelheim am Rhein (DE)

(72) Inventors: Gregory Walter Hiller, Wakefield, MA (US); Matthew Paul Gagnon, Medford, MA (US); Jonathan Coffman, Gaithersbury, MD (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 751 days.

This patent is subject to a terminal disclaimer.

(21) Appl. No.: 17/355,325

(22) Filed: Jun. 23, 2021

(65) Prior Publication Data

US 2021/0317395 A1 Oct. 14, 2021

Related U.S. Application Data

(63) Continuation of application No. 16/071,941, filed as application No. PCT/US2017/014814 on Jan. 25, 2017, now Pat. No. 11,104,875.

(60) Provisional application No. 62/331,619, filed on May 4, 2016, provisional application No. 62/287,194, filed on Jan. 26, 2016.

(51) Int. Cl.
| | |
|---|---|
| *H04M 1/02* | (2006.01) |
| *C07K 16/00* | (2006.01) |
| *C12M 1/00* | (2006.01) |
| *C12M 1/06* | (2006.01) |
| *C12N 5/00* | (2006.01) |
| *C12N 5/071* | (2010.01) |
| *C12P 21/02* | (2006.01) |
| *G06F 1/16* | (2006.01) |
| *G09F 9/30* | (2006.01) |

(52) U.S. Cl.
CPC .............. *C12M 23/58* (2013.01); *C07K 16/00* (2013.01); *C12M 23/40* (2013.01); *C12M 27/02* (2013.01); *C12M 29/10* (2013.01); *C12N 5/0018* (2013.01); *C12N 5/0682* (2013.01); *C12P 21/02* (2013.01); *C07K 2317/24* (2013.01)

(58) Field of Classification Search
None
See application file for complete search history.

(56) References Cited

U.S. PATENT DOCUMENTS

| 2011/0086411 A1 | 4/2011 | Grillberger et al. |
| 2011/0212493 A1* | 9/2011 | Hirschel ................ C12M 29/10 435/235.1 |

FOREIGN PATENT DOCUMENTS

| WO | 2002050251 | 6/2002 |
| WO | 2015003012 A2 | 1/2015 |

OTHER PUBLICATIONS

International Search Report for PCT/US2017/014814 mailed Mar. 29, 2017.
Van Lier et al., "Long-term semi-continuous production of recombinant baculovirus protein in a repeated (fed-)batch two-stage reactor system", 1996, Enzyme and Microbial Technology, vol. 18, pp. 460-466.

* cited by examiner

*Primary Examiner* — Robert M Kelly
(74) *Attorney, Agent, or Firm* — Mary Breen Smith

(57) ABSTRACT

Methods of protein production in a linked culture and production bioreactor system are provided. Such methods include a culture bioreactor (N−1 bioreactor) linked to production bioreactor (N bioreactor). More specifically, the methods include (a) culturing cells with a gene that encodes the protein of interest in a continuous perfusion culture bioreactor (N−1 bioreactor); inoculating a continuously stirred tank reactor (CSTR) production bioreactor (N bioreactor) with cells obtained from step (a); and culturing the cells in the CSTR production bioreactor under conditions that allow production of the protein of interest.

13 Claims, 22 Drawing Sheets

LINKED PERFUSION TO CONTINUOUS-FLOW STIRRED-TANK REACTOR CELL CULTURE SYSTEM

FIELD OF THE SUBJECT TECHNOLOGY

The subject technology relates to methods of protein production in cultured animal cells, preferably mammalian cells, using a linked bioreactor system including a culture bioreactor (N−1 bioreactor) linked to production bioreactor (N bioreactor). More specifically, the subject technology relates to a continuous perfusion culture bioreactor linked to a chemostat or continuous-flow stirred-tank reactor (CSTR) production bioreactor.

BACKGROUND OF THE SUBJECT TECHNOLOGY

Conventional perfusion cell culture systems suffer from disadvantages such as large-volume media consumption, long times to reach peak cell densities and complications with cell retention devices when used at the largest scale.

For example, in the hybrid cell culture systems disclosed in WO 2008091113, multiple CSTR bioreactors are linked in series, each using cell retention devices (e.g., packed bed). The reference suggests that in an ideal system, the last bioreactor in the series would use complete cell retention, but that the earlier bioreactors would allow some cells to pass out of the bioreactor. In the hybrid cell culture system disclosed in WO 2015003012, a single 'nurse' or N−1 bioreactor periodically inoculates multiple N-stage production bioreactors which have cell retention devices. In the hybrid cell culture system disclosed in WO 2015095809, an N−1 perfusion bioreactor is used to prepare an inoculum for a production bioreactor operating in a fed-batch or perfusion mode. However, all the data and examples in this reference suggest that the N−1 is a perfusion bioreactor operating for a short period of time, producing a single inoculum used to inoculate a production bioreactor which operates as a fed-batch. Additionally, nowhere do the authors of this application suggest that the production bioreactor might operate as a chemostat (or CSTR) with no cell retention that produces a continuous harvest to the downstream purification operation.

Cell retention systems are difficult to operate and design for use at the large scale (>1,000 L). For example, nearly any cell retention device that uses a membrane (as do many that are currently in use at large scale) will eventually plug with cell debris. This plugging is more likely to occur with low cell viability cultures as the cells are more fragile, and the particulates that are formed are often similar in size to the pores of the membrane (0.2-5 micron). Additionally, as membranes plug with cell debris they also begin to effectively function as ultrafiltration devices, retaining the high molecular weight product proteins within the bioreactor in a not easily predictable or reproducible manner. This is a disadvantage because in a continuous perfusion bioreactor system it is advantageous to have the product of interest be continuously removed from the bioreactor in the cell-free harvest and delivered to the downstream operation in a consistent manner.

As a result, conventional continuous perfusion cell culture systems usually have working volumes below 2,000 L, and if operated under conditions where productivity is highest (e.g. high viable cell densities and high perfusion rates), require frequent change out of the membrane based cell retention device due to plugging and product retention (ultrafiltration). Additionally, cell retention devices capable of handling very large volumes of cell-free culture harvest can be quite complex (e.g. many moving parts) and expensive, damaging to cells through excessive shear forces, and prone to failure. As the cell retention devices are typically external to the bioreactor, effective cleaning and sterilization can also be challenging at the large scale. These factors can result in high cost of operation, significant loss of productivity and inefficiencies in production of a protein of interest. Therefore, there still remains a need for an alternative cell culture method or system that overcomes the limitations associated with the current conventional perfusion culture systems.

SUMMARY OF THE SUBJECT TECHNOLOGY

The subject technology is illustrated, for example, according to various aspects and embodiments listed below.

In one aspect, the subject technology relates to a method of producing a protein of interest, including: (a) culturing cells comprising a gene that encodes the protein of interest in a culture bioreactor (N−1 bioreactor); (b) inoculating a production bioreactor (N bioreactor) with cells obtained from step (a); and (c) culturing the cells in the production bioreactor under conditions that allow production of the protein of interest. In one or more embodiments relating directly or indirectly to this aspect, the method further comprises step (d) harvesting the protein of interest from the production bioreactor; the culture bioreactor is a continuous perfusion culture bioreactor and the production bioreactor is a continuously stirred tank reactor (CSTR) production bioreactor; the production bioreactor has no cell retention device; volume ratio of the culture bioreactor to the production bioreactor is about 1:1 to about 1:20; volume ratio of the culture bioreactor to the production bioreactor is about 1:1 to about 1:5; volume ratio of the culture bioreactor to the production bioreactor is about 1:5; the inoculation in step (b) is by transferring cells from the culture bioreactor to the production bioreactor; the cell transfer is by cell bleed in continuous or semi-continuous modes; the cell transfer is in semi-continuous mode including the cell transfer once at every period of time from 2 minutes to 24 hours or at any interval therebetween; step (a) optionally alternates between a first and second culture bioreactors to allow for renewal and continuous production of culture cells for use in step (b); the second culture bioreactor is a continuous perfusion culture bioreactor; the production bioreactor operates continuously for a period of greater than 3 weeks; the production bioreactor operates continuously for a period of greater than 4 weeks; the production bioreactor operates continuously for a period of greater than 5 weeks; the production bioreactor operates continuously for a period of greater than 6 weeks; harvesting step (d) is continuous; the cells are CHO cells, HEK-293 cells, VERO cells, NS0 cells, PER.C6 cells, Sp2/0 cells, BHK cells, MDCK cells, MDBK cells or COS cells; the production bioreactor has a volumetric productivity of at least 0.6 grams per liter per day for a period of at least 14 days; the production bioreactor has a volumetric productivity of at least 0.6 grams per liter per day for a period of at least 20 days; the production bioreactor has a volumetric productivity of at least 0.6 grams per liter per day for a period of at least 30 days; the production bioreactor has a product residence time of about 1 to about 10 days; the production bioreactor has a dilution rate of about 1 to about 0.1 volume per day; the production bioreactor is fed with a diluent solution; the diluent solution is water or saline.

In another aspect, the subject technology relates to a linked culture process, including: (a) culturing cells comprising a gene that encodes the protein of interest in a culture bioreactor (N−1 bioreactor); (b) inoculating a production bioreactor (N bioreactor) with cells obtained from step (a); and (c) culturing the cells in the production bioreactor under conditions that allow production of the protein of interest. In one or more embodiments relating directly or indirectly to this aspect, the linked culture process further includes step (d) harvesting the protein of interest from the production bioreactor; the culture bioreactor is a continuous perfusion culture bioreactor and the continuous production bioreactor is a continuously stirred tank reactor (CSTR) production bioreactor; the production bioreactor has no cell retention device; volume ratio of the culture bioreactor to the production bioreactor is about 1:1 to about 1:20; volume ratio of the culture bioreactor to the production bioreactor is about 1:1 to about 1:5; volume ratio of the culture bioreactor to the production bioreactor is about 1:5; the inoculation in step (b) is by transferring cells from the culture bioreactor to the production bioreactor; the cell transfer is by cell bleed in continuous or semi-continuous modes; the cell transfer is in semi-continuous mode comprising the cell transfer once at every period of time from 2 minutes to 24 hours or at any interval therebetween; step (a) optionally alternates between a first and second culture bioreactors to allow for renewal and continuous production of culture cells for use in step (b); the second culture bioreactor is a continuous perfusion culture bioreactor; the production bioreactor operates continuously for a period of greater than 3 weeks; the production bioreactor operates continuously for a period of greater than 4 weeks; the production bioreactor operates continuously for a period of greater than 5 weeks; the production bioreactor operates continuously for a period of greater than 6 weeks; harvesting step (d) is continuous; the cells are CHO cells, HEK-293 cells, VERO cells, NSO cells, PER.C6 cells, Sp2/0 cells, BHK cells, MDCK cells, MDBK cells or COS cells; the production bioreactor has a volumetric productivity of at least 0.6 grams per liter per day for a period of at least 14 days; the production bioreactor has a volumetric productivity of at least 0.6 grams per liter per day for a period of at least 20 days; the production bioreactor has a volumetric productivity of at least 0.6 grams per liter per day for a period of at least 30 days; the production bioreactor has a product residence time of about 1 to about 10 days; the production bioreactor has a dilution rate of about 1 to about 0.1 volume per day; the production bioreactor is fed with a diluent solution; the diluent solution is water or saline.

In another aspect, the subject technology relates to a linked culture system, including: a culture bioreactor (N−1 bioreactor) for culturing cells comprising a gene that encodes the protein of interest; and a production bioreactor (N bioreactor) which is linked to the culture bioreactor and receives cells as inoculum from the culture bioreactor, wherein the production bioreactor operates under conditions that allow production of the protein of interest. In one or more embodiments relating directly or indirectly to this aspect, the system is linked to a downstream purification system for harvesting the protein of interest from the production bioreactor; the culture bioreactor is a continuous perfusion culture bioreactor and the production bioreactor is a continuously stirred tank reactor (CSTR) production bioreactor; the production bioreactor has no cell retention device; volume ratio of the culture bioreactor to the production bioreactor is about 1:1 to about 1:20; volume ratio of the culture bioreactor to the production bioreactor is about 1:1 to about 1:5; volume ratio of the culture bioreactor to the production bioreactor is about 1:5; the inoculation is by transferring cells from the culture bioreactor to the production bioreactor; the cell transfer is by cell bleed in continuous or semi-continuous modes; the cell transfer is in semi-continuous mode comprising the cell transfer once at every period of time from 2 minutes to 24 hours or at any interval therebetween; the system includes a second culture bioreactor that operates in parallel with a first culture bioreactor and alternates in producing inoculum for transfer to the production bioreactor; the second culture bioreactor is a continuous perfusion culture bioreactor; the production bioreactor operates continuously for a period of greater than 3 weeks; the production bioreactor operates continuously for a period of greater than 4 weeks; the production bioreactor operates continuously for a period of greater than 5 weeks; the production bioreactor operates continuously for a period of greater than 6 weeks; the harvesting is continuous; the cells are CHO cells, HEK-293 cells, VERO cells, NSO cells, PER.C6 cells, Sp2/0 cells, BHK cells, MDCK cells, MDBK cells or COS cells; the production bioreactor has a volumetric productivity of at least 0.6 grams per liter per day for a period of at least 14 days; the production bioreactor has a volumetric productivity of at least 0.6 grams per liter per day for a period of at least 20 days; the production bioreactor has a volumetric productivity of at least 0.6 grams per liter per day for a period of at least 30 days; the production bioreactor has a product residence time of about 1 to about 10 days; the production bioreactor has a dilution rate of about 1 to about 0.1 volume per day; the production bioreactor is fed with a diluent solution; the diluent solution is water or saline.

In another aspect, the subject technology relates to a protein of interest produced by a method including: (a) culturing cells comprising a gene that encodes the protein of interest in a culture bioreactor (N−1 bioreactor); (b) inoculating a production bioreactor (N bioreactor) with cells obtained from step (a); and (c) culturing the cells in the production bioreactor under conditions that allow production of the protein of interest. In one or more embodiments relating directly or indirectly to this aspect, the method further comprises step (d) harvesting the protein of interest from the production bioreactor; the culture bioreactor is a continuous perfusion culture bioreactor and the continuous production bioreactor is a continuously stirred tank reactor (CSTR) production bioreactor; the production bioreactor has no cell retention device; volume ratio of the culture bioreactor to the production bioreactor is about 1:1 to about 1:20; volume ratio of the culture bioreactor to the production bioreactor is about 1:1 to about 1:5; volume ratio of the culture bioreactor to the production bioreactor is about 1:5; the inoculation in step (b) is by transferring cells from the culture bioreactor to the production bioreactor; the cell transfer is by cell bleed in continuous or semi-continuous modes; step (a) optionally alternates between a first and second culture bioreactors to allow for renewal and continuous production of culture cells for use in step (b); the second culture bioreactor is a continuous perfusion culture bioreactor; the production bioreactor operates continuously for a period of greater than 3 weeks; the production bioreactor operates continuously for a period of greater than 4 weeks; the production bioreactor operates continuously for a period of greater than 5 weeks; the production bioreactor operates continuously for a period of greater than 6 weeks; harvesting step (d) is continuous; the protein of interest is an antibody or a fusion protein; the cells are CHO cells, HEK-293 cells, VERO cells, NSO cells, PER.C6 cells, Sp2/0 cells, BHK cells, MDCK cells, MDBK cells or COS cells; the production bioreactor is fed with a diluent solution; the diluent solution is water or saline.

Additional advantages of the subject technology will become readily apparent to those skilled in this art from the following drawings and the detailed description. The drawings and description are to be regarded as illustrative in nature, and not as restrictive.

BRIEF DESCRIPTION OF THE DRAWINGS

These and other features, aspects, and advantages of the claimed methods, apparatuses, and/or systems are better understood when the following detailed description is read with reference to the accompanying drawings:

DETAILED DESCRIPTION OF THE SUBJECT TECHNOLOGY

Figure 1:
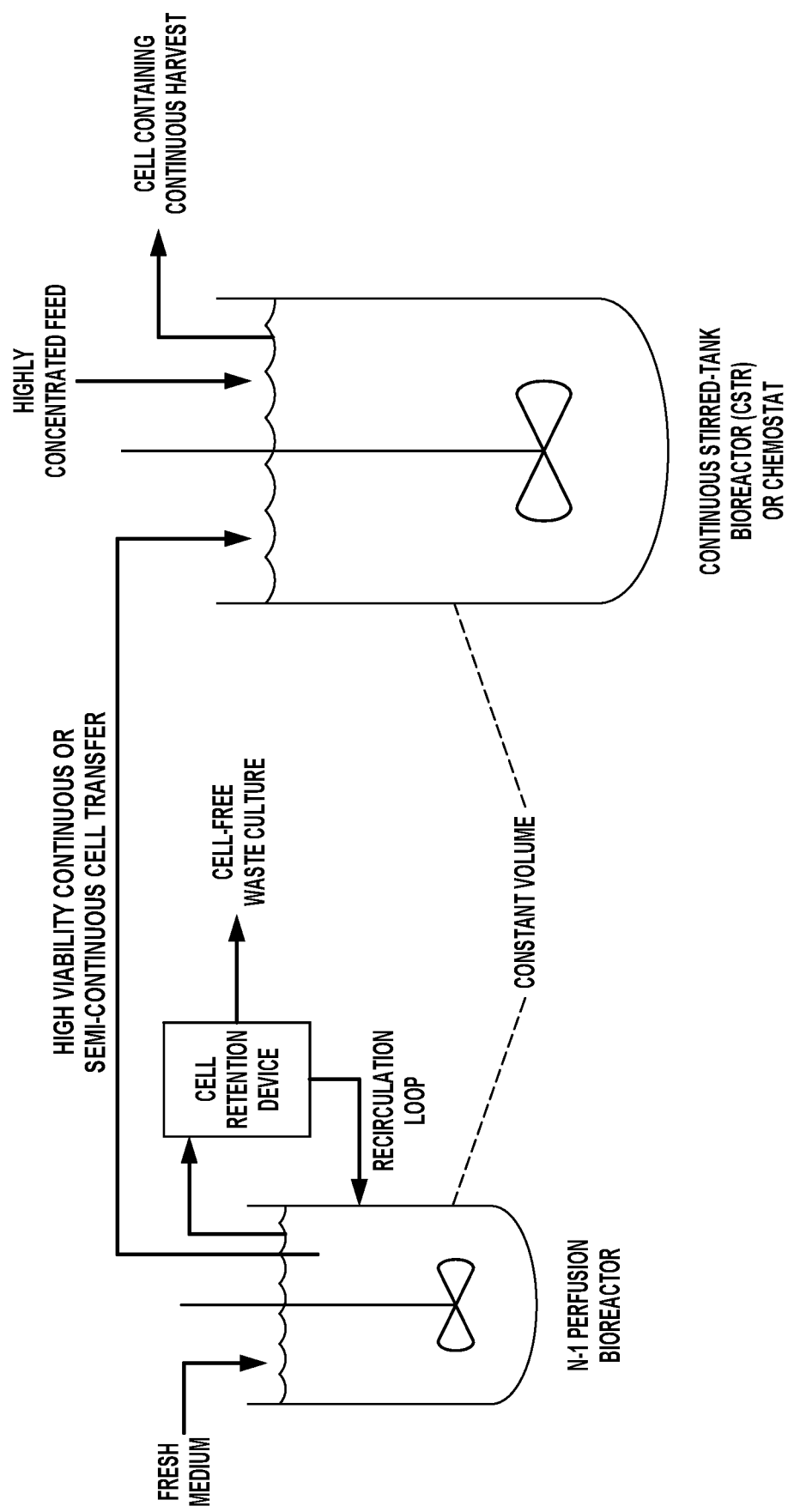
FIG. 1 is an example schematic illustrating the bioreactor configuration, according to an embodiment, described in detail in the experimental section of this application. In this configuration an N−1 bioreactor using perfusion with cell retention continuously supplies cells to a second bioreactor operating as a continuous-flow stirred-tank reactor (CSTR) or chemostat. The CSTR would also receive an additional stream of concentrated nutrient feed. The CSTR would have no cell retention system and would be harvested continuously. In the experiments performed at the bench scale the cell retention device consisted of a 0.2 micron microfiltration hollow cartridge (General Electric CFP-2-E-4X2MA) with a surface area of 850 $cm^2$. Cells were circulated at ~120 mL/minute through the lumen side of a hollow fiber cartridge by a Watson-Marlow peristaltic pump using 6.4 mm ID and 12.7 mm OD tubing.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

To facilitate an understanding of the present subject technology, a number of terms and phrases are defined below:

Definitions

The grammatical articles "one", "a", "an", and "the", as used herein, are intended to include "at least one" or "one or more", unless otherwise indicated. Thus, the articles are used herein to refer to one or more than one (i.e., to at least one) of the grammatical objects of the article. By way of example, "a component" means one or more components, and thus, possibly, more than one component is contemplated and may be employed or used in an implementation of the described embodiments.

The term "about" generally refers to a slight error in a measurement, often stated as a range of values that contain the true value within a certain confidence level (usually ±1σ for 68% C.I.). The term "about" may also be described as an integer and values of ±20% of the integer.

The terms "production bioreactor" or "N bioreactor" or "CSTR bioreactor" or "CSTR production bioreactor" as used interchangeably herein refer to a bioreactor (e.g., continuous-flow stirred-tank reactor (CSTR) that does not utilize a cell retention system or device. The production bioreactor is linked downstream to one or more culture bioreactor(s) and receives inoculum from the culture bioreactor(s). The production bioreactor is uniformly mixed and has a fluid in-flow that is equivalent to the fluid out-flow, therefore, maintaining a near constant volume. Such a production bioreactor will often achieve, although not necessarily, a 'chemically static' or 'steady-state' environment when operating for sufficiently long periods of time, meaning that cell densities and other aspects of the culture (e.g., concentrations of nutrients, etc.) will reach a stable (i.e. steady or static) state, and is therefore also commonly referred to as a 'chemostat'. The fluid in-flow to and/or out-flow from the production bioreactor may be independently continuous or semi-continuous. Such production bioreactor operates continuously for a period or equal or greater than 3, 4, 5, or 6 weeks.

In an embodiment, the CSTR production bioreactor of the subject technology can continue to operate indefinitely or for as long as the cultured cells remain genetically stable. In another embodiment, the CSTR production bioreactor of the subject technology is linked to at least two culture bioreactors which alternate in feeding fresh (i.e., genetically stable) inoculum to the production bioreactor, and as such the production bioreactor continues to run for a long period of time, e.g., equal to or greater than 1, 2, 3, 4, 5, 6 months or for an indefinite period of time so long as the cultured cells that are being fed to it remain genetically stable. Without a cell retention device, the fluid out-flow from the CSTR production bioreactor includes a mixture of cells, cells debris and products. In an embodiment, this fluid out-flow is directed to a cell separation device (e.g., an in-line centrifuge) before being transferred to the next unit operation (e.g., protein A column). The cells and cell debris separated in this fashion from the rest of the fluid out-flow will be discarded and not returned to the production bioreactor.

The terms "cell retention system" or "cell retention device" as used herein refer to a means of selectively retaining viable cells within the bioreactor such that the density of cells in the fluid leaving the bioreactor is lower than the density of cells in the fluid within the bioreactor. In this sense, a cell retention system or device is different from a cell separation device mentioned above.

The terms "culture bioreactor" or "N−1 bioreactor" or "N−1 perfusion bioreactor" as used interchangeably herein refers to a perfusion culture or perfusion bioreactor (e.g., continuous perfusion culture bioreactor) that is used for culturing the cells that will be used for inoculating the production bioreactor. Such culture bioreactor has a cell retention system. There are many different forms of cell retention systems in use in industry. Some of these cell retention systems remove 100% of the viable cells from the liquid leaving the bioreactor system, however many others may remove only some variable fraction of the cells from the liquid leaving the bioreactor system. The liquid transfer to and from the culture bioreactor may be continuous or semi-continuous. Particularly, the cell bleed or transfer from the culture bioreactor to the production bioreactor may be continuous or semi-continuous.

The term "semi-continuous," in the context of liquid transfer to and/or from a bioreactor, as used herein means 'periodic' or refers to a scenario in which liquid (e.g., media alone and/or with cells, cell bleed) is added to and/or removed from the bioreactor once every however long period of time. For example, once every 1, 2, 5, 10, 15, 30, 45 or 60 minutes, or once every hour, or once every 2-3 hours, or once every however long period of time from 1 minutes to 24 hours, a burst of liquid is transferred from and/or to the bioreactor for a period extending from few seconds (e.g., 1 sec., 2 sec., 5 sec. 10 sec., 20 sec. or 60 sec.) to several minutes (e.g. 2 min. 5 min., 10 min., 25 min., 50 min, 120 min. or 240 min.). The term "continuous" in this context refers to a constant or non-periodic liquid transfer. In an embodiment, the rate of cell bleed/transfer from the culture bioreactor to the production bioreactor, either in continuous or semi-continuous mode, is less than the growth rate of the cells in the culture bioreactor. In another embodiment, the rate of cell bleed/transfer from the culture bioreactor to the production bioreactor is from about 0.1 reactor volumes per day (RV/day) to about 1.3 RV/day. In another embodiment, the rate of cell bleed/transfer from the culture bioreactor to the production bioreactor, either in continuous or semi-continuous mode, is less than 1.3 RV/day, or is less than 1.0 RV/day, or is less than 0.8 RV/day, or is less than 0.6 RV/day, or is less than 0.4 RV/day or is less than 0.2 RV/day to about 0.1 RV/day, or a varies within the range of about 0.1 to about 1.3 RV/day.

Perfusion culture of mammalian cells using a cell retention system can offer a significant productivity advantage over batch, fed-batch, or chemostat/CSTR culture. Because cells are retained in the bioreactor system they can be perfused with large volumes of medium and can reach much higher cell densities without the concern for washout that would occur in a CSTR at high dilution rates. Additionally, when a continuous perfusion bioreactor is linked to a continuous downstream purification train, the size of the purification train can be reduced dramatically, which will simplify the overall operations by removing hold steps (and the tanks required), and reducing sampling and analysis of in-process pools. However, perfusion culture of mammalian cells also suffers from many disadvantages, particularly when implemented at large scale (>1,000 L).

Typically most perfusion cultures are operated for long periods of time (>3 weeks). This requires that the cell line be particularly genetically stable so that the cells continue to produce the protein of interest, and that the rate of epigenetic change is sufficiently slow. These long-duration perfusion cultures might be defined as 'sustainable' perfusion cultures, in that the culture can be considered to be able to run as long as the genetic profile of the culture does not drift far enough to negatively affect the productivity or the product quality profile (specifications) of the protein of interest. In such a sustainable perfusion culture, it is necessary to maintain high cellular viability, and this typically necessitates that the cells continue to maintain a non-zero growth rate to continue to divide to make up for cells that die from apoptosis, or shear or oxidative or other stresses. In most cases a finite cell bleed rate (the removal of whole culture broth containing cells) is required to maintain some cell growth and to continuously remove some non-viable biomass from the culture. This 'cell bleed rate' is usually referred to in terms of fraction of the culture volume removed per day, or in terms of reciprocal days. Commonly cell bleed rates are in the 0.05-0.5/day range, with higher rates generally creating conditions for higher cell viability, higher cell growth rates, and more sustainable perfusion systems, but simultaneously fostering lower cell density and generally lower volumetric productivity perfusion cultures.

Additionally, depending upon the cell line, oftentimes CHO (Chinese hamster ovary) cell cultures will have higher specific rates of productivity (mass protein produced per cell per time) when the growth rate of the cells is low. This might be due to a cell devoting more of its resources to continued cell division as opposed to producing the protein of interest when growth rates are high. Fed-batch culture is one of the most common modes of operation used for large-scale production CHO cell cultures and typically will have a short period of cell growth followed by several days in a stationary phase in which most of the product is produced. It follows that there is an advantage to a culture system in which the phases of the culture are separated and the conditions for each phase are optimized; one phase with high cell growth rates to quickly obtain a high cell density, and a separate phase with near zero cell growth rates, but much higher levels of cell specific productivity.

Continuous perfusion systems can be difficult to implement at the large scale (>1,000 L) because cell retention systems do not always perform well at the large scale. Additionally, nearly any cell retention device that uses a membrane (as do many that are currently in use at large scale) will eventually plug with cell debris. This plugging is more likely to occur with low cell viability cultures as the cells are more fragile, and the particulates that are formed are often similar in size to the pores of the membrane (0.2 micron). Therefore, there are advantages to minimizing the size of the vessel in which the perfusion is performed, and keeping the cell viability high to minimize problems with membrane fouling.

As mentioned above, cell particulates can slowly plug membrane-based cell retention systems that utilize micro-filtration membranes on long-term perfusion cultures. It is also possible that as cells lyse and host-cell proteins and the product of interest interact and form higher molecular weight substances. These substances can also contribute to a phenomenon known as gel-layer formation, or product sieving. Under these conditions, cell retention devices utilizing micro-filtration membranes can begin to act as ultra-filtration membranes and selectively retain high molecular weight proteins within the bioreactor system. Since immunoglobulin molecules, one of the most common proteins produced in cell cultures, have relatively high molecular weights (~150,000 Da and above), product sieving has emerged as a major issue with large scale perfusion systems. Oftentimes a continuous perfusion system is linked to a continuous downstream purification system, so it is necessary for the protein of interest to flow out of the bioreactor and for that protein to ideally be of a consistent quantity and quality. The minimization of protein-of-interest retention is particularly important to minimize the size of the downstream system, and is critical when the protein of interest is labile and likely to be degraded by excessive exposure to the conditions inside the bioreactor.

For many of the reasons stated above, there are significant advantages to continuously operating two bioreactors linked together in the following manner and as shown in FIG. 1. The first bioreactor operates as a continuous perfusion culture utilizing high perfusion rates which allow for high cell densities. In this reactor high cell bleed rates will also be used which will maintain high cell growth rates and also therefore high cell viabilities. The second bioreactor, the production bioreactor, can advantageously be 4-5 times the volume of the first bioreactor (typical volume ratios used in large scale facilities for the N−1 and production bioreactor) and will—according to a preferred mode of the subject technology—operate as a chemostat (or continuously stirred tank reactor [CSTR]) reactor with no cell retention system. The terms CSTR or chemostat will be used interchangeably to refer to the production bioreactor throughout this document as in most cases the CSTR will quickly reach a steady-state or 'chemically static' condition in which most or all cell culture parameters will reach nearly constant values. In one embodiment, the volume ratio of the N−1 continuous perfusion culture bioreactor to the CSTR production bioreactor is about 1:1 to about 1:20. In another embodiment, the volume ratio of the N−1 continuous perfusion culture bioreactor to the CSTR production bioreactor is about 1:1 to about 1:5. In another embodiment, the volume ratio of the N−1 continuous perfusion culture bioreactor to the CSTR production bioreactor is about 1:10. In another embodiment, the volume ratio of the N−1 continuous perfusion culture bioreactor to the CSTR production bioreactor is about 1:4.

In a first aspect, the subject technology relates to a method of producing a protein of interest, including: (a) culturing cells including a gene that encodes the protein of interest in a culture bioreactor (N−1 bioreactor); (b) inoculating a production bioreactor (N bioreactor) with cells obtained from step (a); and (c) culturing the cells in the production bioreactor under conditions that allow production of the protein of interest.

In a second aspect, the subject technology relates to a linked culture process, including: (a) culturing cells including a gene that encodes the protein of interest in a culture bioreactor (N−1 bioreactor); (b) inoculating a production bioreactor (N bioreactor) with cells obtained from step (a); and (c) culturing the cells in the production bioreactor under conditions that allow production of the protein of interest.

In a third aspect, the subject technology relates to a linked culture system, including: a culture bioreactor (N−1 bioreactor) for culturing cells including a gene that encodes the protein of interest; and a production bioreactor (N bioreactor) which is linked to the culture bioreactor and receives cells as inoculum from the culture bioreactor, wherein the production bioreactor operates under conditions that allow production of the protein of interest.

In a forth aspect, the subject technology relates to a protein of interest produced by a method including: (a) culturing cells including a gene that encodes the protein of interest in a culture bioreactor (N−1 bioreactor); (b) inoculating a production bioreactor (N bioreactor) with cells obtained from step (a); and (c) culturing the cells in the production bioreactor under conditions that allow production of the protein of interest.

In one or more embodiments relating, directly or indirectly to any of the above aspects, the described method, process or system further includes step (d) harvesting the protein of interest from the production bioreactor; the culture bioreactor is a continuous perfusion culture bioreactor and the production bioreactor is a continuously stirred tank reactor (CSTR) production bioreactor; the production bioreactor has no cell retention device; volume ratio of the culture bioreactor to the production bioreactor is about 1:1 to about 1:20; volume ratio of the culture bioreactor to the production bioreactor is about 1:1 to about 1:5; volume ratio of the culture bioreactor to the production bioreactor is about 1:4; the inoculation in step (b) is by transferring cells from the culture bioreactor to the production bioreactor; the cell transfer is by cell bleed in continuous or semi-continuous modes; the cell transfer is in semi-continuous mode including the cell transfer once at every period of time from 2 minutes to 24 hours or at any interval therebetween; step (a) optionally alternates between a first and second culture bioreactors to allow for renewal and continuous production of culture cells for use in step (b); the second culture bioreactor is a continuous perfusion culture bioreactor; the production bioreactor operates continuously for a period of greater than 3 weeks; the production bioreactor operates continuously for a period of greater than 4 weeks; the production bioreactor operates continuously for a period of greater than 5 weeks; the production bioreactor operates continuously for a period of greater than 6 weeks; the harvesting step (d) is continuous; the cells are for example CHO cells, HEK-293 cells, VERO cells, NSO cells, PER.C6 cells, Sp2/0 cells, BHK cells, MDCK cells, MDBK cells or COS cells or any cell genetically derived therefrom like for example derivatives with specific metabolic conditions and/or selection systems like the glutamine selection, which genetically derived cells and/or metabolic conditions and/or selection systems are in principle known to a person skilled in the art; the production bioreactor has a volumetric productivity of at least 0.6 grams per liter per day for a period of at least 14 days; the production bioreactor has a volumetric productivity of at least 0.6 grams per liter per day for a period of at least 20 days; the production bioreactor has a volumetric productivity of at least 0.6 grams per liter per day for a period of at least 30 days; the production bioreactor has a product residence time of about 1 to about 10 days; the production bioreactor has a dilution rate of about 1 to about 0.1 volume per day.

Non-limiting examples of mammalian cells, which can be used for the present invention are summarized in Table 1.

TABLE 1

Suitable exemplary mammalian production cell lines

| CELL LINE | REFERENCE NUMBER |
|---|---|
| NS0 | ECACC No. 85110503 |
| Sp2/0-Ag 14 | ATCC CRL-1581 |
| BHK21 | ATCC CCL-10 |
| BHK TK− | ECACC No. 85011423 |
| HaK | ATCC CCL-15 |
| 2254-62.2 (BHK-21 derivative) | ATCC CRL-8544 |
| CHO | ECACC No. 8505302 |
| CHO wild type | ECACC 00102307 |
| CHO-DUKX (= CHO duk−, CHO/dhfr−) | ATCC CRL-9096 |
| CHO-DUKX B11 | ATCC CRL-9010 |
| CHO-DG44 | Urlaub et al., Cell 33 (2), 405-412, 1983; Life Technologies A1097101 |
| CHO Pro-5 | ATCC CRL-1781 |
| CHO-S | Life Technologies A1136401; CHO-S is derived from CHO variant Tobey et al. 1962 |
| Lec13 | Stanley P. et al, Ann. Rev. Genetics 18, 525-552, 1984 |
| V79 | ATCC CCC-93 |
| HEK 293 | ATCC CRL-1573 |
| COS-7 | ATCC CRL-1651 |
| HuNS 1 | ATCC CRL-8644 |
| Per. C6 | Fallaux, F.J. et al, Human Gene Therapy 9 (13), 1909-1917, 1998 |
| CHO-K1 | ATCC CCL-61, ECACC 85051005 |
| CHO-K1/SF | ECACC 93061607 |
| CHO-K1 GS | glutamine synthetase (GS) deficient cells derived from CHO-K1 |
| CHOZN GS | SAFC ECACC 85051005, cells derived from CHO-K1 |

Said production cells are cultivated preferentially under conditions that allow the cells to proliferate. Furthermore, said production cells are cultivated preferentially under conditions, which are favorable for the expression of the desired gene(s) and/or the protein of interest. The protein of interest is than isolated from the cells and/or the cell culture supernatant. Preferably the protein of interest is recovered from the culture medium as a secreted polypeptide, or it can be recovered from host cell lysates if expressed without a secretory signal.

Culture from the N−1 bioreactor will enter the production bioreactor at a continuous and fixed flowrate which will be equivalent to the cell bleed rate of the N−1 bioreactor. Additionally, the production bioreactor will have a continuous feed of nutrient media as the cells in that bioreactor will continue to metabolize, produce product, and potentially undergo some limited cell division. The working volume of both bioreactors would likely be held constant, so the effective dilution rate of the production bioreactor would be determined by the flows of the N−1 continuous cell bleed and the continuous feed of nutrient media and any pH-controlling titrant added directly to the production reactor.

Such a bioreactor system might mitigate many of the problems of current continuous perfusion bioreactors. The perfusion bioreactor and its associated cell retention system will likely be significantly simpler to operate as they will operate at approximately one-fifth scale of the production bioreactor. If gel-layer/product sieving occurs in the cell retention device, this will only increase the overall productivity of the system as now the protein of interest generated in the N−1 bioreactor will flow into the production bioreactor and eventually to the downstream purification process rather than to drain with cell-free permeate as shown in FIG. 1.

In situations where the cell line is not sufficiently genetically stable for long term operation, a second N-1 bioreactor will be used that would start periodically with an inoculum of fresh cells expanded from frozen vials and once that bioreactor has come up to the proper cell density the second N-1 bioreactor could take the place of the first N-1 bioreactor while the first N-1 bioreactor is taken down for cleaning and re-sterilization. The cell density in the N-1 culture bioreactor(s) may vary according to the size of the production bioreactor is it linked to. In some embodiments, the cell density in the culture bioreactor is about $10 \times 10^6$ per liter or more, or is about $20 \times 10^6$ per liter or more, or is about $40 \times 10^6$ per liter or more, or is between $10 \times 10^6$ and $200 \times 10^6$ per liter, or is between $40 \times 10^6$ to $120 \times 10^6$ per liter or is at a specific density within any of these ranges. Since the cell division in the production bioreactor is likely to be low, this would allow for a semi-continuous renewal of the cells producing the protein with a genetically younger cell population. The production bioreactor might then be able to operate continuously with minimal interruption and at high cell density and high productivity, producing a feed stream to downstream purification operations with consistent quality parameters for months at a time. Therefore, in one embodiment, the linked cell culture system of the subject technology includes an N-1 continuous perfusion culture bioreactor (N-1 bioreactor) in which cells that include a gene that encodes the protein of interest are cultured before they are transferred to a CSTR production bioreactor without a cell retention device. In another embodiment, the linked cell culture system of the subject technology includes two N-1 culture bioreactors that operate in alternative to produce cultured cells for transfer to a CSTR production bioreactor. In another embodiment, the N-1 continuous perfusion culture bioreactor(s) of the subject technology operate in the following modes: hi-end pH-control of glucose (HIPDOG), described in Biotechnol Bioeng. 2011 June; 108(6):1328-37, or high-end pH-control of perfusion rate (HIPCOP) described in co-pending application WO 2016/196261, entitled "Cell-Controlled Perfusion in Continuous Culture" for a description of this method.

Cell lines with higher specific productivities at low growth rates, or cells that require different cell culture environmental conditions to be highly productive or produce product with particular product quality characteristics, should particularly benefit from such a bioreactor configuration as it is likely that the growth rate in the production bioreactor will be quite low and more similar to the conditions that are typically achieved in the later stages of a fed-batch bioreactor. This also might mean that the product quality of the protein of interest produced in such a linked continuous N-1 to CSTR production bioreactor might be more similar to the product quality of fed-batch produced protein. Therefore, in an embodiment, the CSTR production bioreactor operates under conditions that promote highest cell productivity which might in some cases also be conditions which slow cell growth. To achieve high productivity conditions, known chemicals that improve per cell productivity but slow or stop growth can be added to the CSTR production bioreactor. Alternatively, the CSTR bioreactor may be made to operate, for example, under low or high pH, or low temperature (with additions of Cu, low Ca, additions of galactose, etc.) that are beneficial for getting cells to produce protein with particular quality attributes, but those same conditions do not allow for high rates of cell growth.

As mentioned above, the cell specific productivity might in some cases be inversely related to the growth rate of the cells in the production (CSTR) bioreactor. A CSTR operating at a high dilution rate should result in higher growth rates as inhibitory metabolites would be more effectively flushed out of the bioreactor. The dilution rate of the CSTR will be dependent upon the cell bleed rate from the N-1 continuous perfusion bioreactor, and the rate of feed and any titrant used for pH control directly entering the CSTR. Manipulating the concentration of the feed medium to the CSTR would allow for a balance of optimal growth, nutrient availability, and inhibitor metabolite flushing from the system. Multiple factors, many of which are interrelated might contribute to the maximum productivity of the combined N-1 continuous perfusion and CSTR system, including the cell density and growth rates of the cells in both bioreactors, the perfusion rates in the N-1, and the dilution rates of the CSTR. It is advantageous to manipulate the dilution rate of the CSTR by using a single concentrated feed media, and to dilute this media with water, or water mixed with a saturated saline solution as needed. Control of the dilution rate with variable concentration feed media might also allow for control over the residence time of the recombinant protein produced from the system. High dilution rates would result in low product residence times and might be advantageous for highly labile proteins.

Many in industry are currently exploring the use of cell retention/perfusion bioreactors as the production system for mammalian cell cultures. Such systems increase volumetric productivity and make possible continuous downstream purification trains. Since as with a continuous perfusion bioreactor as the production bioreactor, the linked N-1 perfusion bioreactor to chemostat or CSTR production bioreactor described in the present work would continue to generate a constant stream of product to the downstream operation, the advantages of a smaller and continuous downstream operation could continue to be realized.

In addition, the subject technology relates to a protein of interest produced by a method as described above. Such protein of interest includes, but is not limited to an antibody or a fusion protein, such as a Fc-fusion proteins. Others can be for example enzymes, cytokines, lymphokines, adhesion molecules, receptors and derivatives or fragments thereof, and any other polypeptides and scaffolds that can serve as agonists or antagonists and/or have therapeutic or diagnostic use. Other recombinant proteins of interest are for example, but not limited to insulin, insulin-like growth factor, hGH, tPA, cytokines, such as interleukins (IL).

A preferred recombinant secreted therapeutic protein is an antibody or a fragment or derivative thereof. Thus, the invention can be advantageously used for production of antibodies such as monoclonal antibodies, multispecific antibodies, or fragments thereof, preferably of monoclonal antibodies, bi-specific antibodies or fragments thereof. Antibody fragments include e.g. "Fab fragments" (Fragment antigen-binding=Fab). Fab fragments consist of the variable regions of both chains, which are held together by the adjacent constant region. These may be formed by protease digestion, e.g. with papain, from conventional antibodies, but similar Fab fragments may also be produced by genetic engineering. Further antibody fragments include F(ab')2 fragments, which may be prepared by proteolytic cleavage with pepsin.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilized. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins are known to the person skilled in the art. Preferred secreted recombinant therapeutic antibodies according to the invention are bispecific antibodies. Bispecific antibodies typically combine antigen-binding specificities for target cells (e.g., malignant B cells) and effector cells (e.g., T cells, NK cells or macrophages) in one molecule. Examplary bispecific antibodies, without being limited thereto are diabodies, BiTE (Bi-specific T-cell Engager) formats and DART (Dual-Affinity Re-Targeting) formats. Also anticipated in the context of the present invention are minibodies. By minibody, the skilled person means a bivalent, homodimeric scFv derivative.

The recombinant secreted therapeutic protein, especially the antibody, antibody fragment or Fc-fusion protein is preferably recovered/isolated from the culture medium as a secreted polypeptide. It is necessary to purify the recombinant secreted therapeutic protein from other recombinant proteins and host cell proteins to obtain substantially homogenous preparations of the recombinant secreted therapeutic protein. As a first step, cells and/or particulate cell debris are removed from the culture medium or lysate. Further, the recombinant secreted therapeutic protein is purified from contaminant soluble proteins, polypeptides and nucleic acids, for example, by fractionation on immunoaffinity or ion-exchange columns, ethanol precipitation, reverse phase HPLC, Sephadex chromatography, and chromatography on silica or on a cation exchange resin such as DEAE. Methods for purifying a heterologous protein expressed by host cells are known in the art.

EXAMPLES

Example 1

Application of the Continuous N-1 Perfusion Bioreactor Feeding a CSTR Production Bioreactor (at the 1-2 Liter Scale) in Producing a Humanized IgG with CHO Cells FIG. 1 shows the diagram of the two-stage linked bioreactor system used in the experiment. For the purposes of the experiment the N-1 perfusion bioreactor working volume including the perfusion loop (cell-retention system) was 1.25 liters and the working volume of the production bioreactor was 1.0 liters. At the full scale in an industrial setting, it is contemplated that the N-1 bioreactor would be approximately one fifth the volume of the production (CSTR or chemostat) bioreactor. For this reason the experimental bioreactors were operated to simulate such a volume ratio. This means that the majority of cell bleed (~81% of the total cell bleed) from the N-1 perfusion bioreactor was sent to drain. Only the appropriate volume (~19% of the total) of the cell bleed was pumped into the production bioreactor. The only exception to this rule occurred in the first 3 days of operation of the production (CSTR) bioreactor in which all of the cell bleed from the N-1 was added to the production bioreactor. This allowed the production bioreactor to come up to a high density slightly faster than would have otherwise occurred.

Figure 2A:
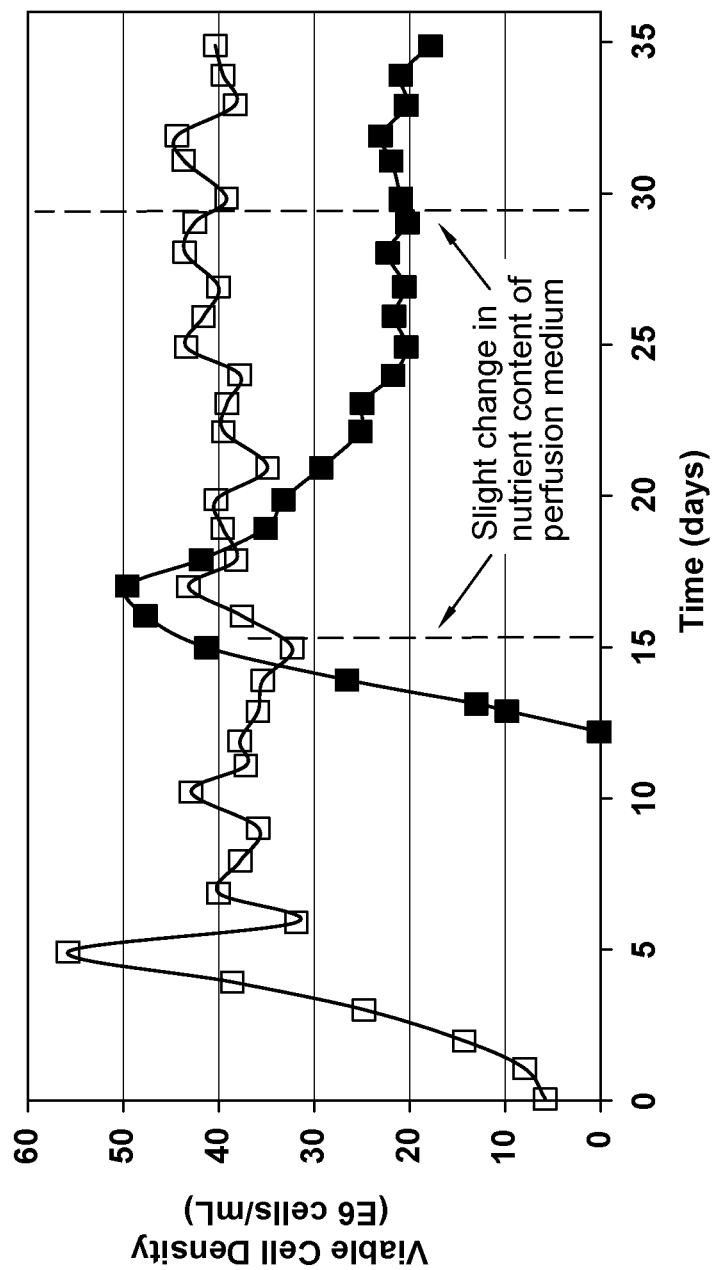
FIG. 2A is a plot showing the viable cell density as measured by trypan blue exclusion as described in the experimental section of this application. Open squares represent cell density in the N−1 perfusion reactor. Solid squares represent cell density in the CSTR or production bioreactor. Dashed vertical lines represent step changes to a slightly different perfusion medium composition flowing into the N−1 perfusion reactor as indicated in Table 2.
Figure 3:
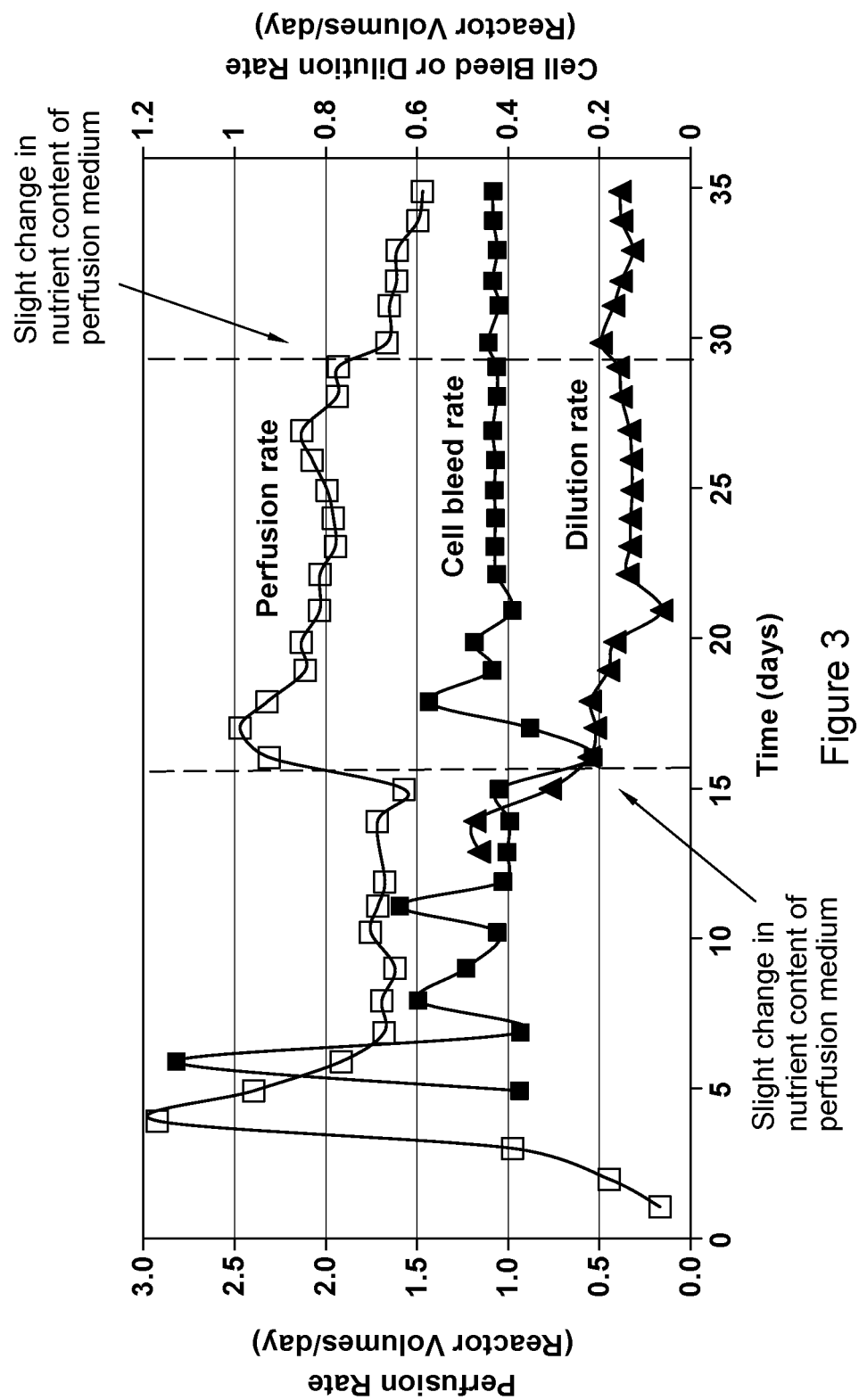
FIG. 3 illustrates the perfusion rate and the cell bleed rate of the N−1 bioreactor, and the dilution rate of the production (CSTR) bioreactor. The perfusion rate (open squares) is listed in reactor volumes (RV) per day and corresponds to the left hand y-axis. The perfusion rate is the volume of medium that flowed into the N−1 perfusion bioreactor per day. The cell bleed rate (solid squares) is the volume of culture containing cells removed (continuously) from the N−1 perfusion bioreactor each day and corresponds to the right hand y-axis. The dilution rate (solid triangles) is the fraction of volume containing cells (the only stream leaving the CSTR) that is removed (continuously) from the production (CSTR) bioreactor each day and corresponds to the right hand y-axis.

FIG. 2a initially shows only the N-1 perfusion bioreactor cell density. That density quickly increased to the target density of approximately $40 \times 10^6$ viable cells/mL, after which the cell bleed was initiated and manually adjusted over the course of the culture to achieve a constant viable cell density in the N-1 bioreactor of approximately $40 \times 10^6$ viable cells/mL. As shown in FIG. 3, for the majority of the experiment the cell bleed rate of the N-1 perfusion bioreactor was approximately 0.4/days, or 0.4 reactor volumes removed per day.

The N-1 perfusion bioreactor used a feedback mechanism based on pH which allows the culture to determine its own rate of perfusion. The perfusion medium contained a small amount of sodium-L-lactate (listed in Table 2).

TABLE 2 lists details of the compositions of the perfusion media that was used for the N-1 bioreactor.

TABLE 2

The compositions of the perfusion media in the N-1 bioractor.

| Medium | Used from days | Total AA (mM) | Glucose (g/L) | Sodium-L-Lactate (g/L) | Osmotic Strength (mOsm) |
|---|---|---|---|---|---|
| Rich N-1 perfusion | 1-15 and 29-35 | 70 | 5.3 | 1.8 | 335 |
| Lean N-1 perfusion | 15-29 | 60 | 4.2 | 1.7 | 319 |

The culture 'signals' a lack of available glucose by beginning to take up lactic acid from the bulk culture. The removal of lactic acid by the cells from the bulk culture fluid results in a rise in the pH of the bioreactor which in turn activates a pump which delivers perfusion medium containing glucose to the N-1 perfusion bioreactor, thereby increasing the perfusion rate of the culture (a level controller removes cell-free medium [permeate] from the culture through the shell side of the hollow fiber cell retention device to maintain a constant bioreactor volume). When the cells in the culture begin to take up the excess glucose that is being delivered, some fraction of it is converted to lactic acid by the cells which then suppresses the bulk culture pH as it is secreted from the cells, which in turn causes the pH controller to deactivate the perfusion medium addition pump (also in turn deactivating the permeate pump). This control scheme occurs again and again as a cycle every few minutes during the course of an experiment. See co-pending application No. WO 2016/196261, entitled "Cell-Controlled Perfusion in Continuous Culture" for a description of this method. Briefly, in the method described in co-pending application No. WO 2016/196261, the pH trigger for turning on and off the perfusion pumps, fresh medium and permeate pumps, is set at a predetermined value. This predetermined value is about pH 7 (e.g., between 6.8-7.4). The medium comprises glucose, L-lactate and a specified ratio of amino acid to glucose. The described method also comprises adding L-lactate to a fresh perfusion medium used in the continuous culture process. The L-lactate present in the perfusion medium is in an amount of about 0.1 g/L to 7.0 g/L. Alternatively or in addition, the L-lactate present in the perfusion medium is in an amount of about 1 to 4 g/L, about 1 to 3 g/L, or about 1 to 2.5 g/L. In a preferred embodiment, the L-lactate is sodium L-lactate or potassium L-lactate. In another embodiment, the lactate used in the perfusion medium may be a D/L mixture of sodium or potassium lactate. In cases where a D/L mixture of lactate is used, enough mixture is added to the perfusion medium such that the amount of L-lactate would be identical to that used when only L-lactate was used. In an embodiment, additional sodium bicarbonate is added to the perfusion medium instead of, or in addition to, L-lactate. A typical cell culture medium contains about 1.0 to 2.5 grams/L of sodium bicarbonate. In an embodiment, the perfusion medium for the N-1 perfusion bioreactor of the subject technology has an additional 1 to 3 grams/L of sodium bicarbonate to achieve a total concentration of about 2 to 5.5 grams/L of sodium bicarbonate. The perfusion medium in this method requires at least glucose, L-lactate (or alternatively or in addition, sodium bicarbonate) and amino acids. The concentration of glucose is about 0.5 to about 40 g/L. The concentration of L-lactate is about 0.1 to about 7.0 g/L. The concentration of sodium bicarbonate is about 1 to 5.5 grams/L. The ratio of moles of glucose to amino acids is between about 0.25 and 1.0. In HIPCOP model, as the cell density increases (FIG. 2a) the cells effectively 'request' additional perfusion medium on a more and more frequent basis resulting in a ramp up of perfusion rate (FIG. 3).

A similar control scheme for the addition of glucose to fed-batch cultures has been described in the literature (Biotechnol Bioeng. 2011 June; 108(6):1328-37). The N-1 perfusion culture uses this technology of high-end pH-control of perfusion rate (HIPCOP) for the entire duration of the experiment. When necessary or useful, the CSTR or production bioreactor also uses a similar technique of glucose limitation to control lactic acid formation. In the CSTR when the pH rises as a result of lactic acid uptake by the cells, a pump is triggered to add a concentrated nutrient feed containing glucose, or a feed containing pure glucose dissolved in water. Table 3 lists the feed media or pure glucose solution that was used as part of this hi-end pH-control of glucose (HIPDOG) strategy.

TABLE 3 lists details of the compositions of the concentrated feed media that was delivered to the CSTR (chemostat) on-demand via the high-end pH-control system (HIPDOG) when that system was in operation from days 12-19, and again from days 29-33.

TABLE 3

The compositions of the concentrated feed media.

| Medium | Used from days | Total AA (mM) | Glucose (g/L) | Sodium-L-Lactate (g/L) | Osmotic Strength (mOsm) |
|---|---|---|---|---|---|
| Lean Feed to production CSTR | 12-16 | 380 | 80 | 0 | ~1105 |
| Rich Feed with high glucose to production CSTR | 16-17, 18-19 | 600 | 120 | 0 | ~1702 |
| Rich Feed with low glucose to production CSTR | 17-18 | 600 | 80 | 0 | ~1480 |
| Concentrated glucose feed to production CSTR | 29-33 | 0 | 300 | 0 | ~1666 |

The HIPDOG strategy was used to control lactic acid formation for the CSTR only from days 12-19, and from days 29-33. Additional fixed rate feeding of concentrated nutrient solutions occurred to the CSTR from days 19-35. The rate of addition of these feeds was determined by occasionally analyzing off-line samples for residual amino acid levels in the CSTR and changing the feed rate to the CSTR if excess (above 30 millimolar) total amino acids or depleted (below 30 millimolar) total amino acids were detected. Using the feeding schemes described in this paragraph we believe that the cells in the CSTR were not likely overly limited with respect to glucose availability, nor were they limited for availability of any particular amino acid. When steady-state, or near steady-state conditions are reached in the N-1 and CSTR combined reactors between about day 25-28 and also day 32-35, from FIG. 3 we can see that the cell bleed of the N-1 bioreactor is approximately 0.43/day and the dilution rate of the production CSTR reactor is approximately 0.13-0.15/day. In some embodiments, the dilution rate of the production bioreactor is about 0.05-0.4 or about 0.1-0.3 or about 0.15-0.2/day. Due to the ⅕th volume ratio that was simulated with these two linked bioreactors it can be calculated that the cell bleed from the N-1 perfusion reactor is contributing approximately 53-62% of the volume of liquid entering the CSTR, and the remainder consists of concentrated media or glucose feeds.

The line from the N-1 perfusion bioreactor to the production bioreactor (CSTR or chemostat) was first connected and opened on about day 12 which allowed cells to begin to flow into the CSTR. In an industrial setting there would be no strong driver to delay the start of the CSTR. Presumably it could be started at the first time point that cell bleed is removed from the N-1 perfusion bioreactor. In the current experiment the CSTR was started after it was believed that the N-1 had reached a near steady-state condition.

From day 12 to 15 (the first 3 days of the CSTR operation) all of the cell bleed from the N-1 was pumped into the production (CSTR) bioreactor. This would likely be the normal start up method at industrial scale in which the N-1 bioreactor is approximately ⅕th the volume of the CSTR. In the small scale experimental system however the volume of the bioreactors are nearly identical and this means that a much larger number of cells were added to the CSTR system in the first 3 days of its operation than could likely occur at the large scale. This was performed at the small scale to accelerate reaching a high density in the CSTR, but should have negligible effect on the final steady-states reached in the combined bioreactor system. On day 15 the flow from the N-1 perfusion to the production CSTR reactor was adjusted to accurately simulate a 1:5 volume ratio.

Figure 2B:
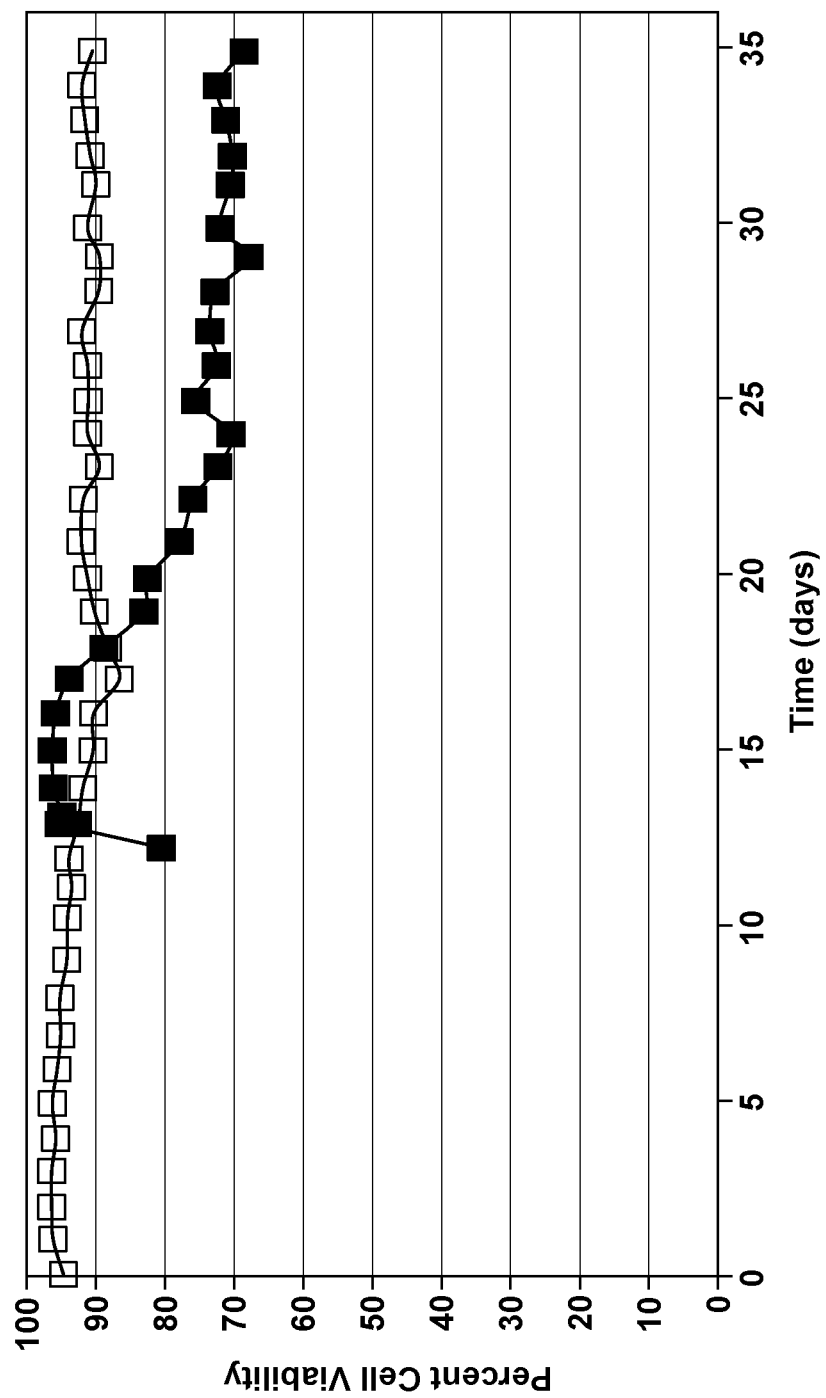
FIG. 2B is a plot showing the percent viable cells as measured by trypan blue exclusion. Open squares represent cell viability in the N−1 perfusion reactor. Solid squares represent cell viability in the CSTR or production bioreactor.
Figure 4:
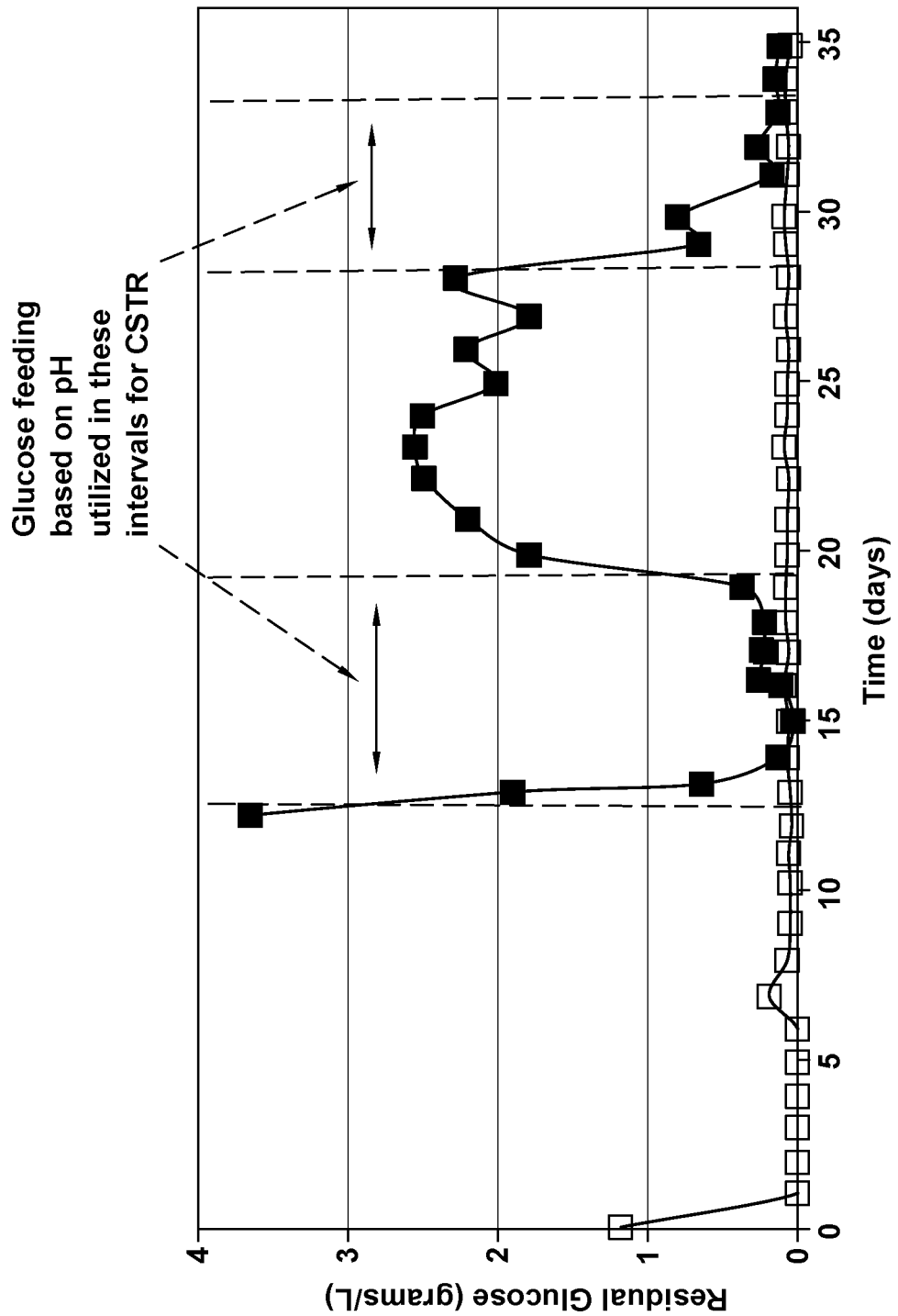
FIG. 4 is a plot showing the residual glucose concentration in the N−1 (open squares) and production (CSTR, solid squares) bioreactors.
Figure 5:
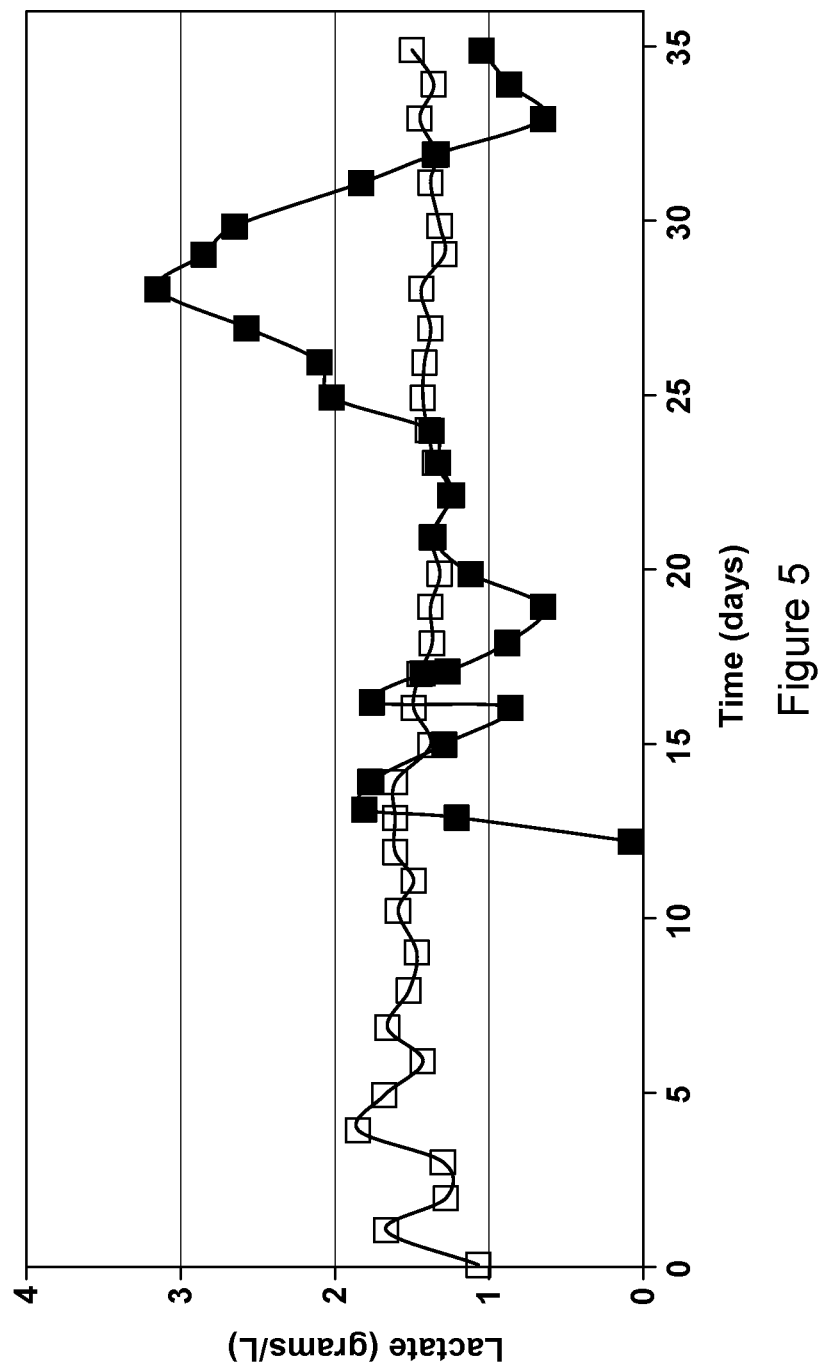
FIG. 5 is a plot showing the lactate concentration in the N−1 (open squares) and production (CSTR, solid squares) bioreactors.
Figure 6:
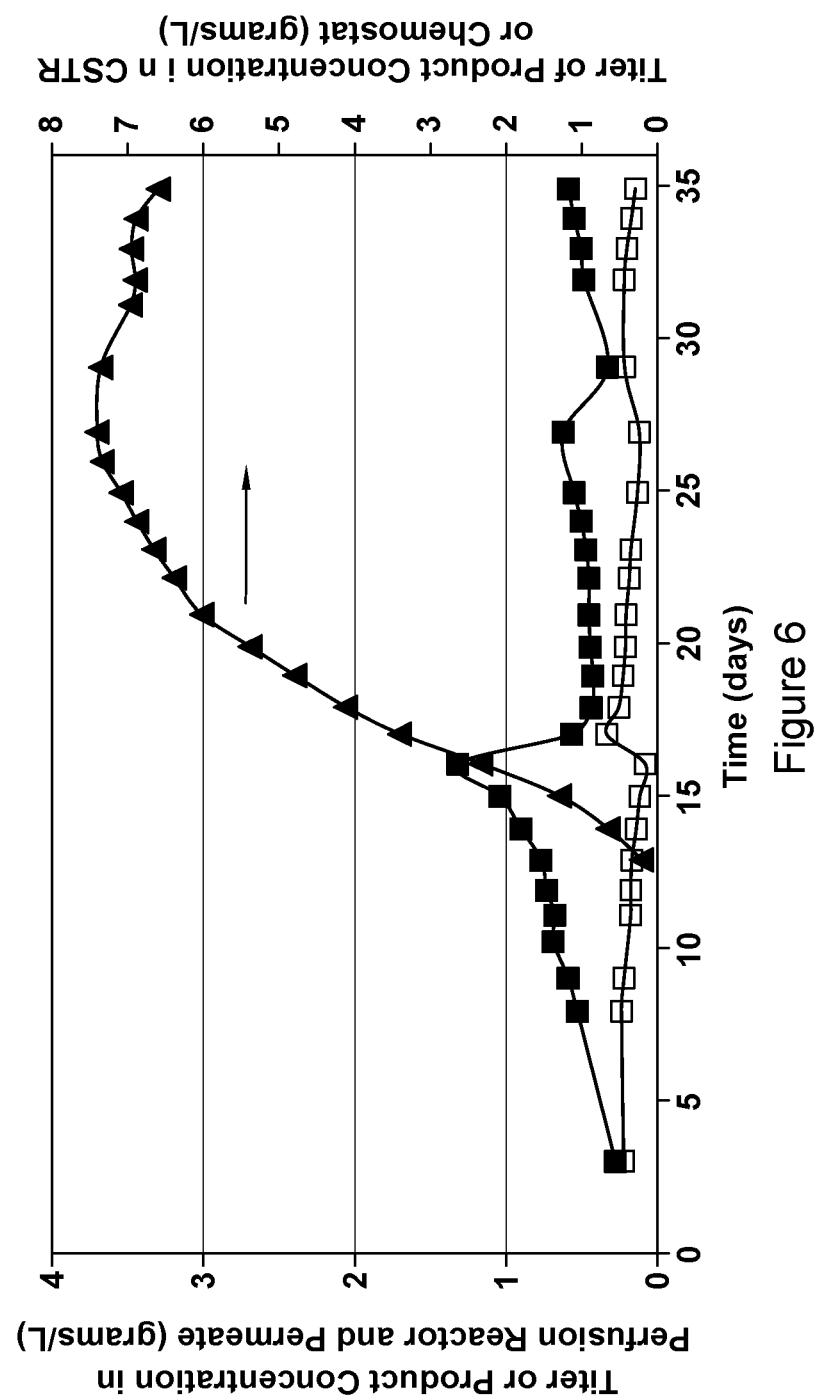
FIG. 6 is a plot showing the antibody or product concentration in the bulk fluid of the N−1 bioreactor (solid squares), in the permeate leaving the N−1 bioreactor system (open squares), and in the bulk fluid and leaving the production bioreactor continuously (CSTR, solid triangles).
Figure 7:
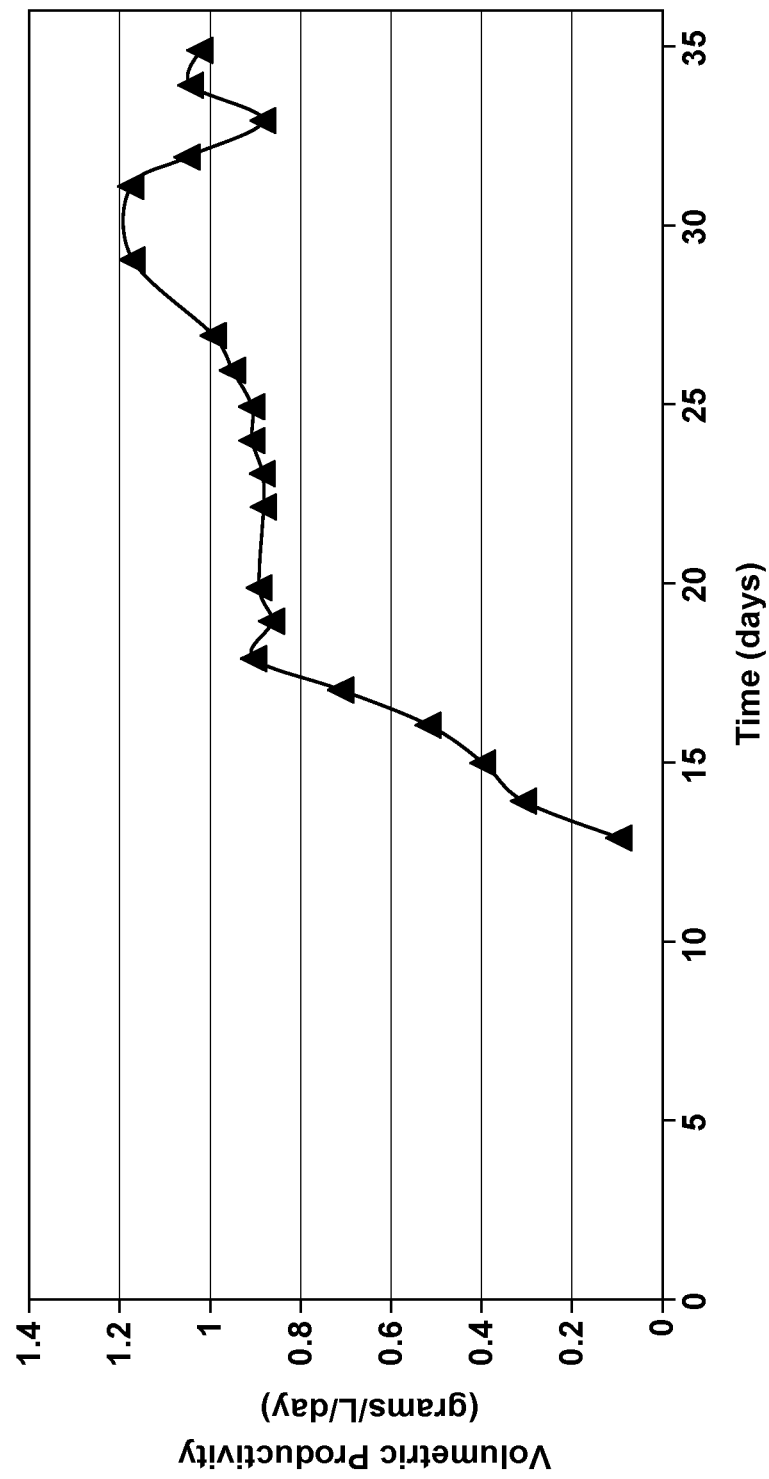
FIG. 7 is a plot showing the volumetric productivity of the CSTR production bioreactor in grams product produced per reactor volume per day (solid triangles).

Steady-state with respect to most parameters, cell density (FIG. 2a), cell viability (FIG. 2b), bioreactor volume flows (FIG. 3), metabolite concentrations (FIGS. 4 and 5), and product concentrations and volumetric productivities (FIGS. 6 and 7) was first reached on about day 23. At this point the volumetric productivity of the CSTR was approximately 0.9 grams/liter reactor volume/day. This volumetric productivity was maintained or slightly exceeded for the next 12 days (FIG. 7). While some product sieving, or selective retention of antibody product occurs in the N-1 bioreactor (solid and open squares of FIG. 6) across the hollow-fiber cell retention device, a simple mass balance calculation considering the volume of liquid per day entering the CSTR from the N-1 bioreactor (~65% of the total volume entering the CSTR) and its product concentration (0.4-0.6 grams/L), and the volume per day and concentration of product (6.4-7.4 grams/L) leaving the CSTR on day 23 shows that the volumetric productivity calculated for the CSTR is primarily (~93-98%) due to generation of product in the CSTR. TABLE 4 lists details of the compositions of the concentrated feed media that was delivered to the production (CSTR) reactor at various fixed rates via manual manipulation from days 19-35.

TABLE 4

The compositions of the concentrated feed media in the production reactor.

| Medium | Used from days | Total AA (mM) | Glucose (g/L) | Sodium-L-Lactate (g/L) | Osmotic Strength (mOsm) |
|---|---|---|---|---|---|
| Rich Feed with very low glucose to production CSTR | 19-27 | 600 | 50 | 0 | ~1313 |
| Lean Feed to production CSTR | 27-29 | 380 | 80 | 0 | ~1105 |
| Lean Feed with low glucose to production CSTR | 29-35 | 380 | 50 | 0 | ~939 |

It is of value to compare the steady-state volumetric productivity of the combined bioreactor system (~0.9 grams/liter/day) on day 23 to that of the N-1 perfusion bioreactor operating independently as a production bioreactor. Using the product concentrations and volumes leaving the N-1 perfusion bioreactor, and assuming that a downstream operation can capture material from both streams (cell-free permeate and cell-containing cell bleed) the volumetric productivity of the N-1 perfusion bioreactor on day 23 is approximately 0.46 grams/liter/day, roughly half of the volumetric productivity of the combined bioreactor system (0.9 grams/liter/day). Additionally, the medium consumption rate of the N-1 perfusion bioreactor operating independently on day 23 is approximately 1.95 reactor volumes/day. The combined N-1/CSTR system medium consumption rate (including both the N-1 perfusion medium and the concentrated nutrient feeds to the CSTR system) is only 0.44 reactor volumes/day (based on the volume of the CSTR), less than one quarter of the medium consumption rate of the N-1 perfusion bioreactor operating independently as a production bioreactor.

It should be noted that while in this particular experiment the high-end pH-control of perfusion rate (HIPCOP) was used for the N-1 perfusion bioreactor, and the hi-end pH-control of glucose (HIPDOG) strategy was intermittently used in the CSTR production bioreactor, these control modes are to be regarded as optional in carrying out the subject technology. Alternative or additional control mechanisms may be applicable by taking into consideration the metabolic conditions needed for each cell type to be cultured by the methods and system of the subject technology. For example, various CHO cell lines and other mammalian cell expression systems have distinctive cellular metabolisms that might make the use of glucose limiting techniques optional for the linked bioreactor described herein.

Example 2

IgG (Immunoglobulin G) Production

Utilizing Cell Line B—a Glutamine-Synthetase Expression System CHO (Chinese Hamster Ovary) Cell Line in Making an IgG Protein The experimental design of the two-stage linked bioreactor system used in this example is identical to that used in example 1. For the purposes of the experiment the N-1 perfusion bioreactor working volume including the perfusion loop (cell-retention system) was 1.36 liters and the working volume of the production bioreactor (CSTR) was 1.1 liters. In an industrial setting, the N-1 bioreactor is contemplated to be approximately one fifth the volume of the production (CSTR or chemostat) bioreactor. For this reason (in a similar manner to example 1), the experimental bioreactors were operated to simulate such a volume ratio at the beginning of the experiment. Later in the experiment (day 32) the experimental bioreactor configurations were changed in a way such that they simulate a volume ratio of 1:10, and changed yet again on day 44 to simulate a volume ratio of 1:20. In each of these cases, solely for the purpose of simulating the theoretical bioreactor volume differences, a large fraction of the cell bleed from the N-1 continuous perfusion bioreactor was sent to drain instead of going into the production bioreactor. As the volume ratio simulation was increased from 1:5 to 1:10 and then later to 1:20, a larger fraction of the volume of cells coming from the N-1 perfusion bioreactor was sent to drain.

Various process control parameters and set-points (pH, dissolved oxygen, temperature, etc.) are listed in table 5 for the bioreactors used in these experiments.

TABLE 5

Operating parameters and control set-points used in the N-1 continuous perfusion and CSTR production biareactors.

| Parameter | N-1 Perfusion Bioreactors | Production CSTR Bioreactors |
|---|---|---|
| Inoculation density (viable cells/mL) | $1.2 \times 10^6$ | 0 |
| Temperature(° C.) Controlled with electric heating blankets | 36.5 | |
| High-end pH Set-Point | 7.125 (Controlled using HIPCOP technology [see text]) | 7.125 (Controlled using HIPDOG technology prior to day 22 or 26 [see text]) |
| Low-end pH Set-Point (using 1 M sodium carbonate/potassium carbonate [molar ratio of 0.94 sodium: 0.06 potassium]) | 7.075 (used only during first three days of culture) | 7.075 |
| Dissolved Oxygen Set-Point (percent of air saturation) | 40 ± 10% | |
| Oxygen Delivery Method | Pure oxygen delivered through 15 micron sintered-steel sparge tip | |
| Carbon Dioxide Removal Method | Air delivered through drilled-hole sparger (large bubbles) 7 × 1 mm holes Flow rate between 2.5 to 4X of the 15 micron sparge oxygen | |
| Working Volume (liters) | 1.36 | 1.10 |
| Agitation | Single Rushton impeller (6 cm diameter) operating at 275 RPM ~90 W/m$^3$ power/unit volume | |

As mentioned in Table 5 a dual sparging strategy was used in which the majority of oxygen to the culture was delivered through a 15 micron sintered steel sparger using pure oxygen, and the majority of removal of carbon dioxide was accomplished by sparging atmospheric air through a drilled hole (7×1 mm holes) sparger producing large bubbles. The sparge rate of the air through the drilled hole sparger was varied between 2.5 to 4 times the volume of oxygen used in the 15 micron sparger. This strategy was sufficient to control dissolved oxygen at the 40% of air saturation set point, and to keep dissolved carbon dioxide levels between 5-13% for the first 13 days of the cultures, and between 4-8% from day 13 on (when the majority of key data was collected).

For this example two N-1 perfusion bioreactors were operated and each of these reactors independently supplied a continuous cell source to one production bioreactor operating as a continuous-flow stirred tank reactor (CSTR). The target steady-state viable cell density for the $1^{st}$ N-1 perfusion reactor was ~$40 \times 10^6$ cells/mL, and for the $2^{nd}$ N-1 perfusion reactor was ~$80 \times 10^6$ cells/mL. The N-1 perfusion bioreactors were started eight days before the first cells were transferred to the production bioreactors. The production bioreactors (the CSTR's) were started at full volume, meaning that the bioreactors were completely full of medium when the first cell bleeds from the N-1 perfusion bioreactors started to flow into the production bioreactors. The production bioreactors were started at full volume partly because the experimental plan for the linked bioreactor system experiment was designed to explore several different effective dilution rates in the production bioreactors (CSTR's), and to attempt to collect steady-state data for each of those conditions. This type of experiment (a dilution rate study) is generally facilitated by exploring high dilution rates first before moving to lower dilution rates that typically require longer time periods to reach steady-state conditions. Also, low dilution rates are likely to result in lower viability cultures and could result in long lag times for cells to react when later moving to higher dilution rates with more favorable culture conditions. For this reason, high dilution rates in the production bioreactors were investigated first.

Starting the production bioreactor at full volume (prior to the addition of cells from the N-1 perfusion bioreactor) is probably not the optimal way to initiate such a culture. There may be a benefit from a medium and facility utilization standpoint to start the bioreactor at partial volume so that when the first material is removed from the production bioreactor (when the bioreactor is full) the cell density, concentration of product of interest, and potentially product quality of the protein is already near to the final steady-state value. This optimal starting volume (which depends upon the growth and product production kinetics of any particular cell line) can be determined by routine experimentation and computer modeling simulations. The optimal starting volume of the production bioreactor also depends upon the optimal (highest productivity and practical operating conditions) steady-state conditions of the N-1 perfusion and CSTR combined system.

Figure 8:
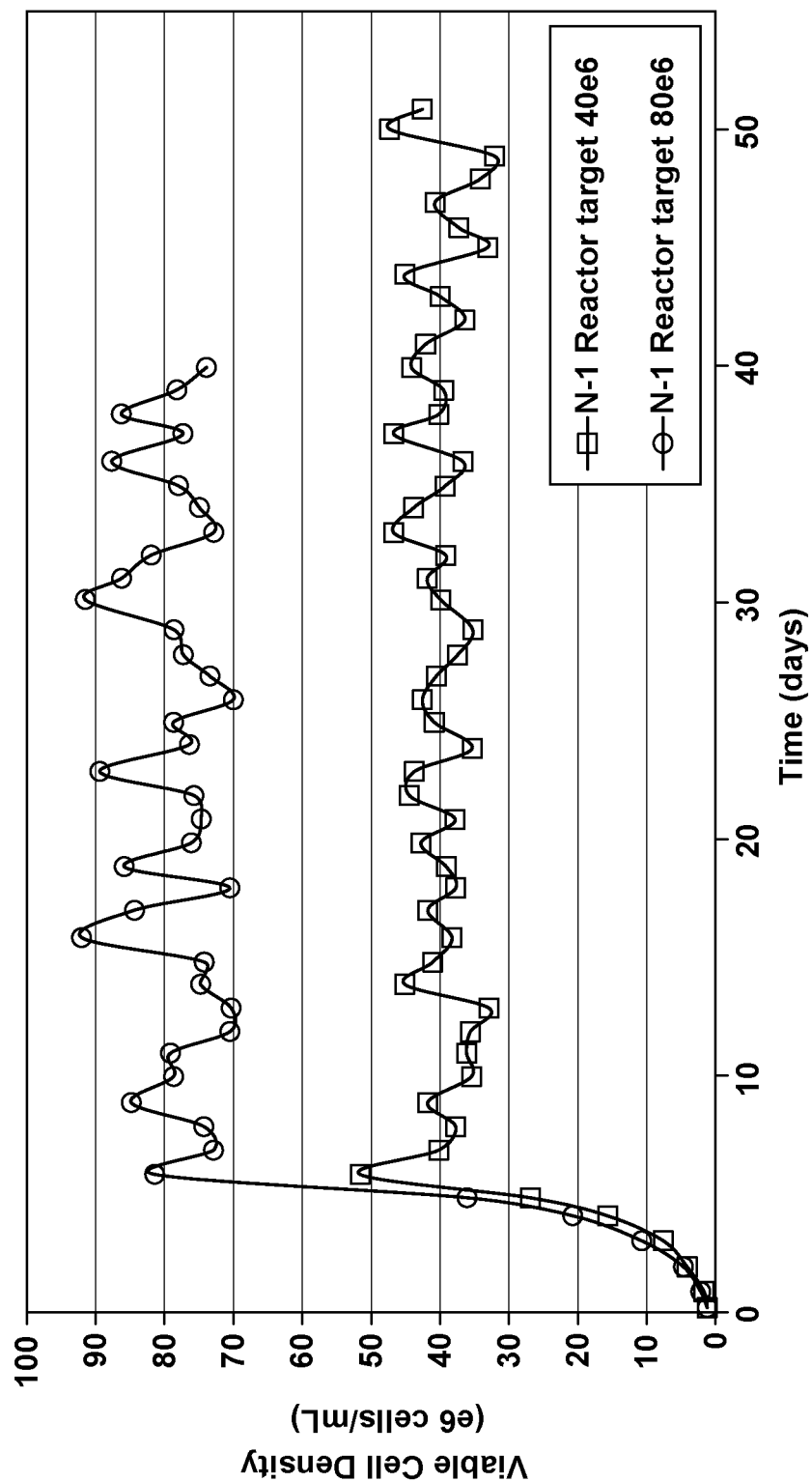
FIG. 8 is a plot showing the cell density of two N−1 perfusion bioreactors as a function of time. The target steady-state viable cell density for the $1^{st}$ N−1 perfusion reactor was ~40×10$^6$ cells/mL, and for the $2^{nd}$ N−1 perfusion reactor was ~80×10$^6$ cells/mL. As described in more detail in Example 2, in this configuration, each of these N−1 perfusion bioreactors independently feeds into a separate CSTR production bioreactor.
Figure 10:
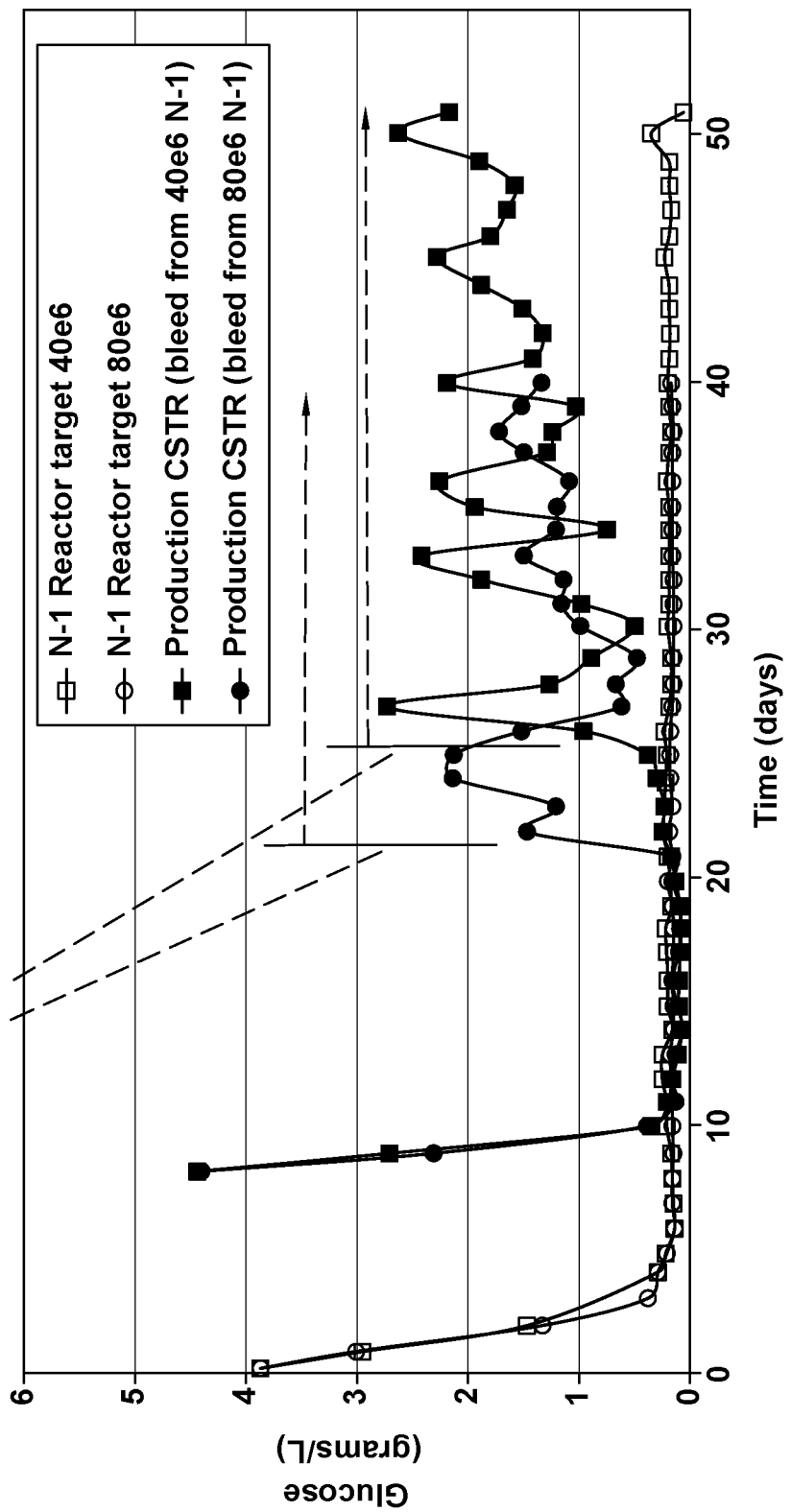
FIG. 10 is a plot showing the residual glucose as a function of time for the two continuous perfusion bioreactors (open symbols) and for the two production bioreactors operating as CSTR's (solid symbols) each linked to one of the perfusion bioreactors.
Figure 11:
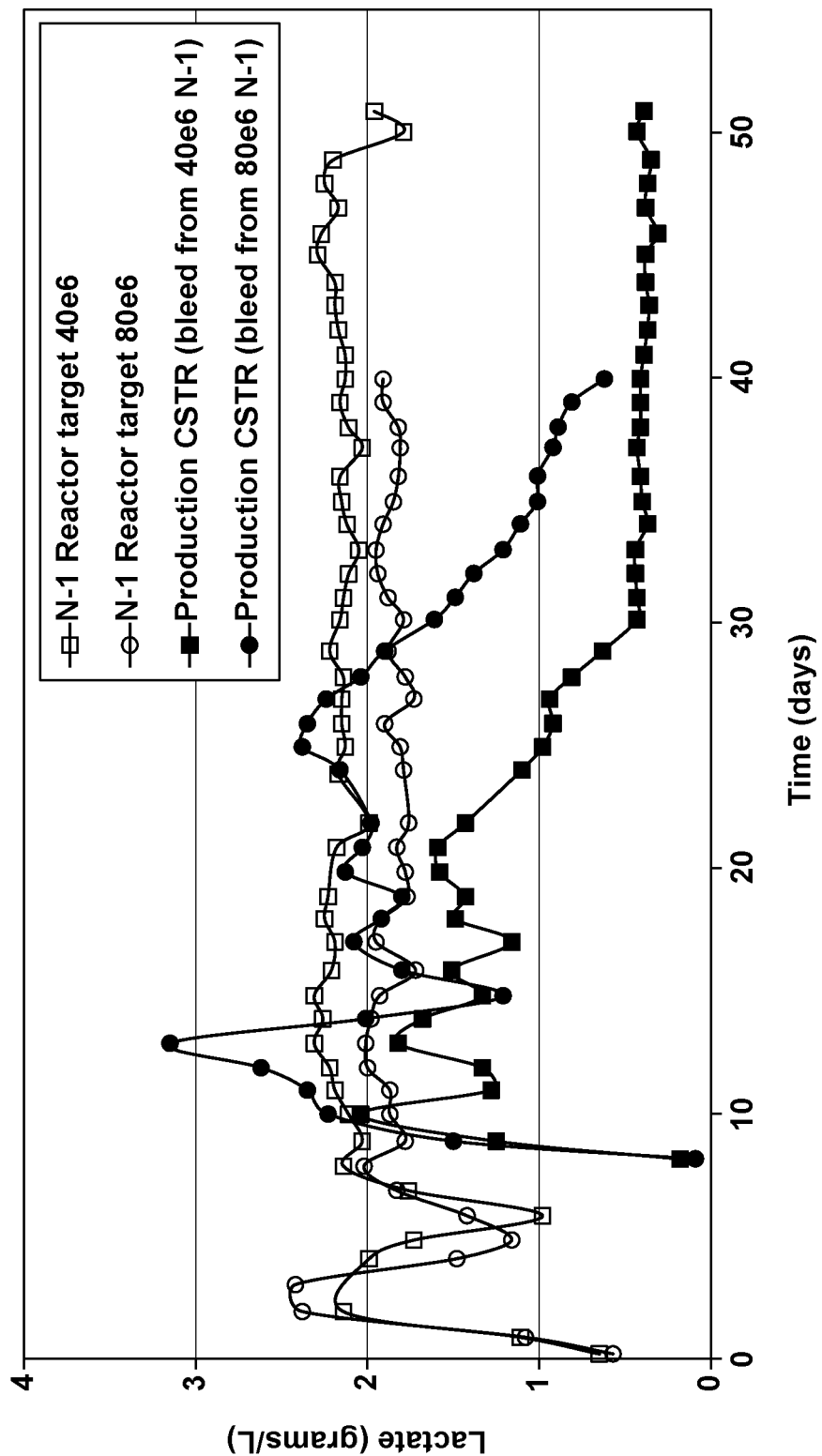
FIG. 11 is a plot showing the lactate concentration as a function of time for the N−1 continuous perfusion bioreactors (open symbols) and for the production bioreactors operating as CSTR's (solid symbols).
Figure 12:
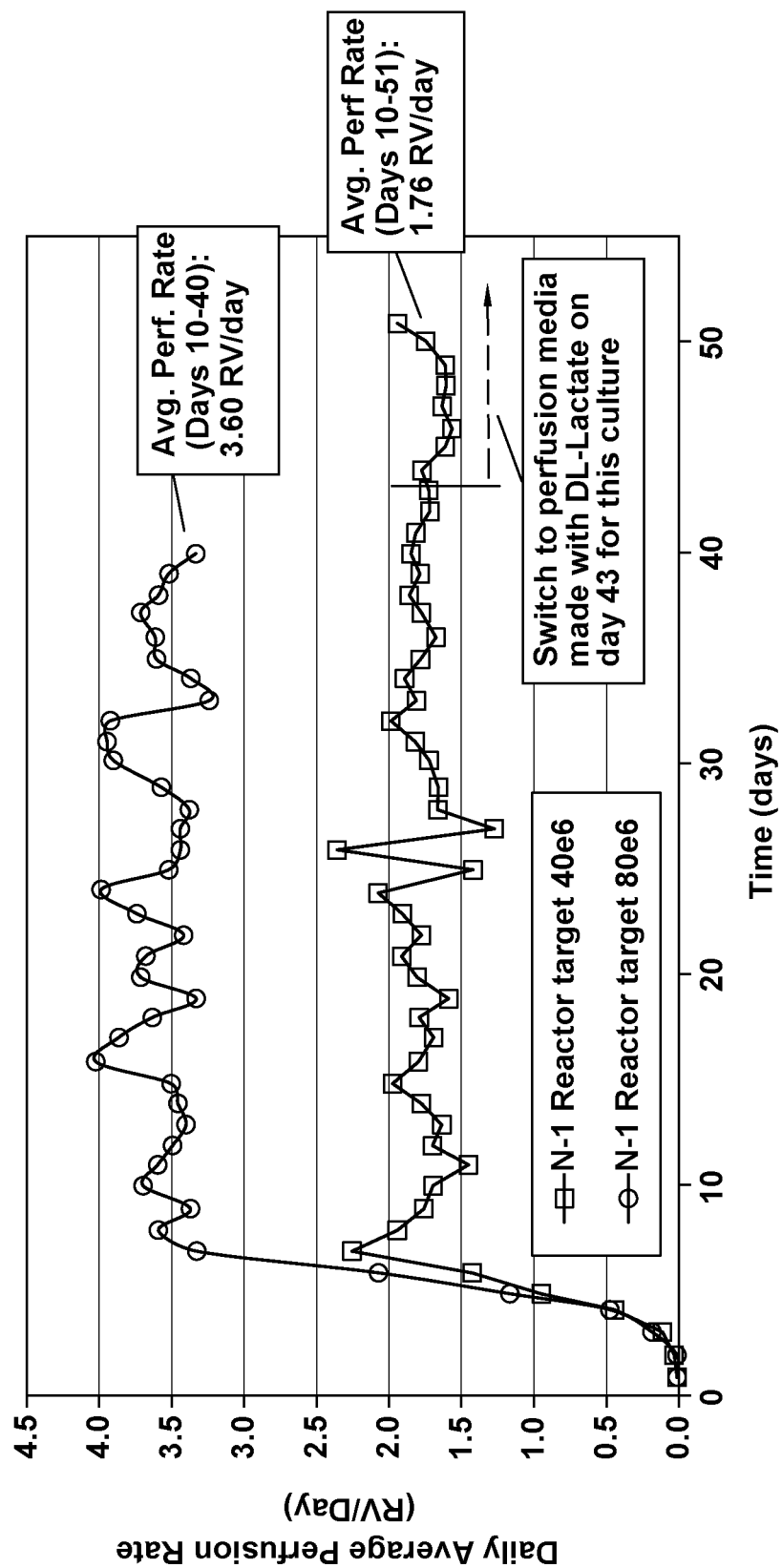
FIG. 12 is a plot showing the perfusion rate of N−1 continuous perfusion bioreactors—perfusion rate is controlled by the cells using the HIPCOP technology as described in Example 2.

The two N-1 continuous perfusion bioreactors were inoculated at ~$1.2 \times 10^6$ viable cells/mL from cells maintained in Erlenmeyer shake flasks. The bioreactors initially operated in a batch mode (no perfusion). As the cell density increased (FIG. 8) the glucose concentration fell from around 4 grams/L to below 0.4 grams/L (FIG. 10) on day 3. Simultaneously lactate initially accumulated to slightly over 2 grams/L (FIG. 11). Once the glucose level fell to a sufficiently low concentration, the cells began to take up lactic acid from the culture (day 3), raising the pH of the bulk fluid and triggering the addition of perfusion medium (and the simultaneous removal of cell-free permeate through the cell retention system to maintain the bioreactor working volume constant). See the application No. 62/246,774, entitled "Cell-Controlled Perfusion in Continuous Culture" for a description of this method. This method will be referred to as HIgh-end pH Control Of Perfusion (HIPCOP). The cells continued to control and ramp up their own perfusion rate over the next several days (FIG. 12). After approximately day 8 the perfusion rate stabilized for the two bioreactors and remained relatively stable for the duration of the experiment. During the entire experiment the perfusion rate was controlled by the HIPCOP technology. The average perfusion rate for the target $40 \times 10^6$ cells/ml N-1 perfusion bioreactor from day 10 to day 51 can be calculated to be 1.76 reactor volumes per day (this is defined as the total volume of medium pumped into the bioreactor). The average perfusion rate for the target $80 \times 10^6$ cells/ml N-1 perfusion bioreactor from day 10 to day 40 can be calculated to be 3.60 reactor volumes per day. Beyond day 5 the residual glucose level in both N-1 bioreactors was very near zero for the entire experiment as is typical of bioreactors operating with the HIPCOP technology (FIG. 10).

Figure 9:
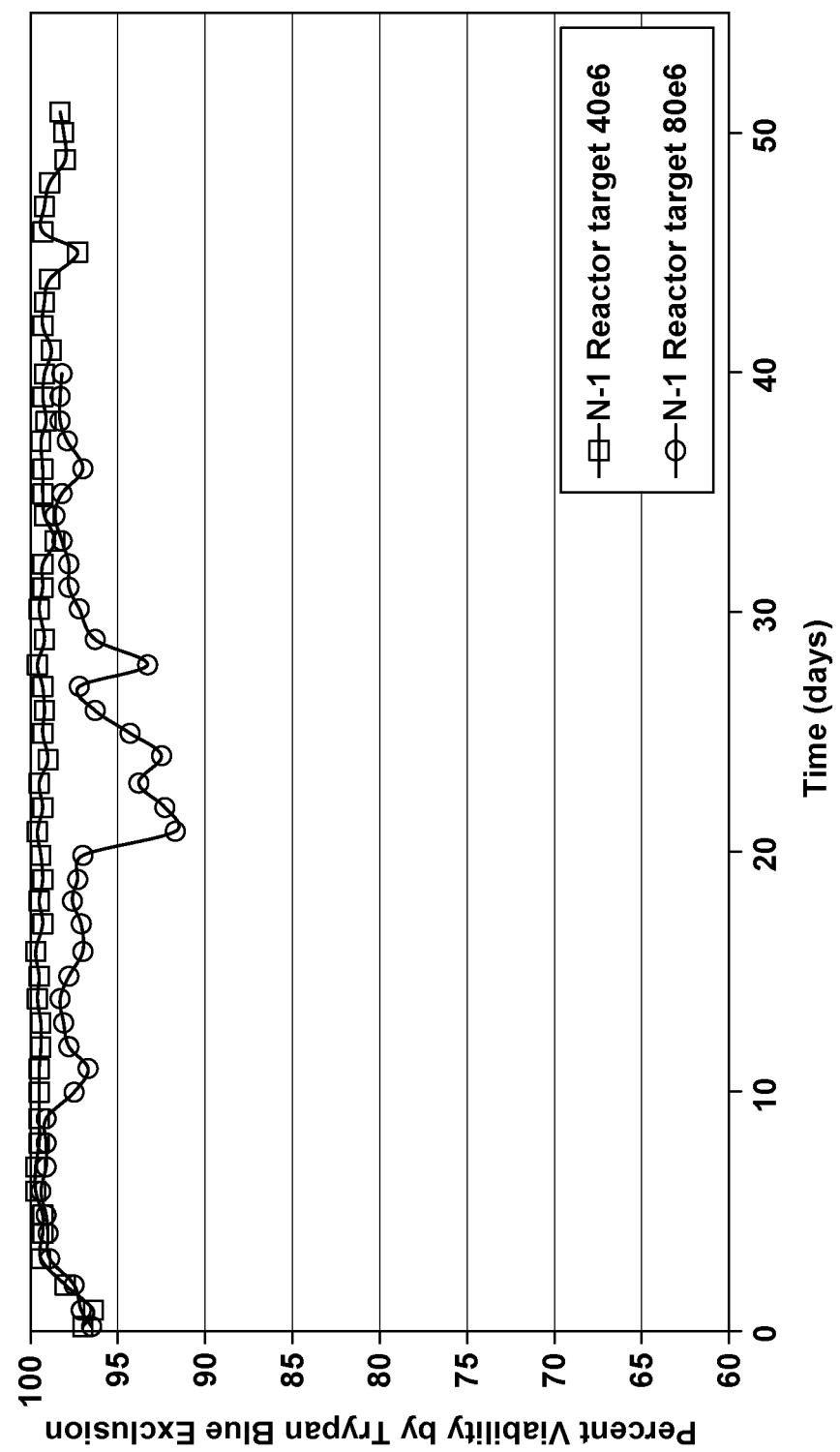
FIG. 9 is a plot showing the cell viability of two N−1 perfusion bioreactors as a function of time.

On day 6 the direct removal of cell containing culture (the cell bleed) from the N-1 perfusion reactors was initiated. Most long-duration or sustainable perfusion bioreactor operations require some amount of cell bleed to help maintain cell viability in the bioreactor and keep the overall levels of inert biomass from becoming problematic. The cell viability for the N-1 perfusion bioreactors is shown in FIG. 9. The viability for both cultures was high, above 90% for the entire length of the experiment. The viability was slightly lower in the higher density culture. This might have been due to slightly higher shear forces that were likely experienced due to the almost twice as high gas sparging levels that were necessary to maintain dissolved oxygen and carbon dioxide in appropriate ranges in the higher density culture.

Figure 13:
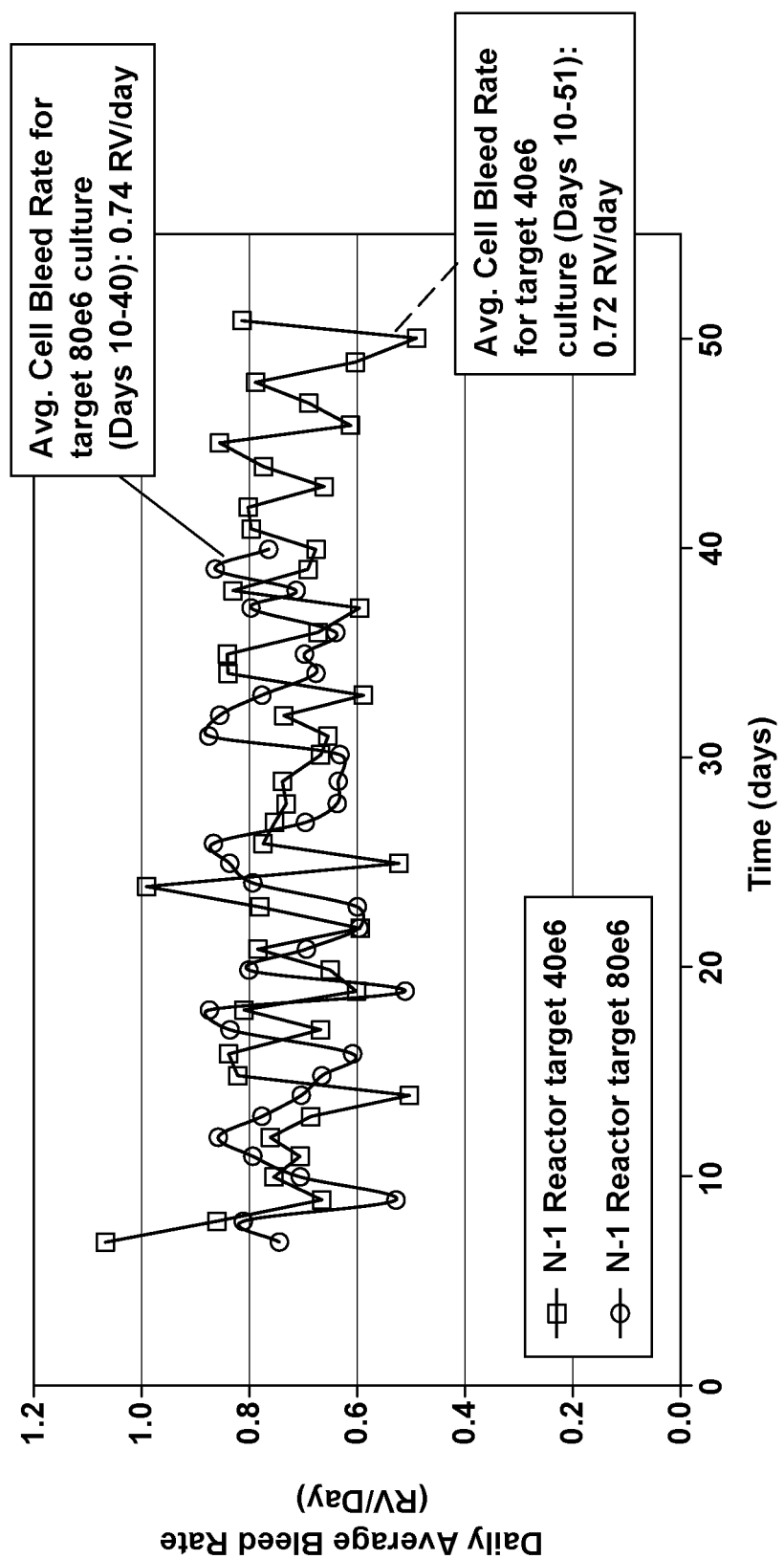
FIG. 13 is a plot showing the cell bleed rates of the two N−1 continuous perfusion bioreactors.

From days 6 to 8 the cell bleed was directed to waste as it was thought that for the purposes of the experiment it might be easier to initiate the production reactors (CSTR's) when the cell bleed rate and cell densities in the N-1 perfusion cultures had stabilized. The cell bleed rates were adjusted daily in an attempt to keep the cell densities of the N-1 perfusion reactors (FIG. 8) as close as possible to their target densities of 40 and $80 \times 10^6$ cells/mL. The cell bleed rates are indicated in FIG. 13. After day 8 the manual adjustments were minor and the average cell bleed rate for the target $40 \times 10^6$ cells/ml N-1 perfusion bioreactor from day 10 to day 51 can be calculated to be 0.72 reactor volumes per day. The average cell bleed rate for the target $80 \times 10^6$ cells/ml N-1 perfusion bioreactor from day 10 to day 40 can be calculated to be 0.74 reactor volumes per day.

On day 8 the cell bleeds from the N-1 perfusion reactors were directed into the two independently operating production bioreactors (CSTR's). As mentioned earlier in the text, the correct volume of cell bleed was directed into the production bioreactors such that a 1:5 volume ratio of N-1 to production bioreactor was simulated. In an industrial application in which the trajectories of cell densities and cell bleed rates, and the final optimal operating conditions for the linked bioreactors would be known before the start of the experiment, it would likely be most efficient to immediately direct the cell bleed (from the first day the cell bleed is started) to the production (CSTR) reactor.

Figure 14:
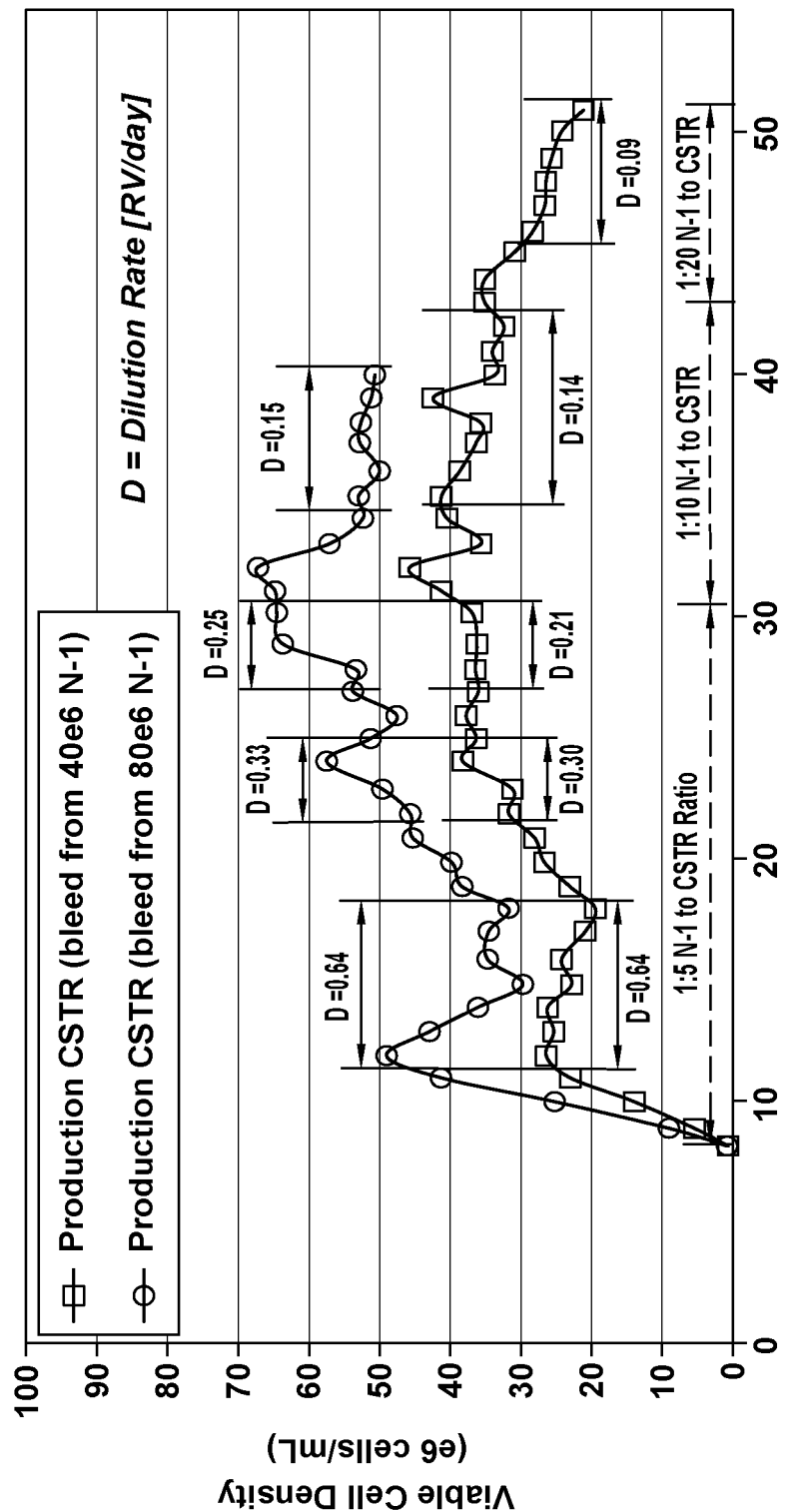
FIG. 14 is a plot showing the viable cell densities as a function of time in the production bioreactors operating as continuous-flow stirred-tank reactors (CSTR's). Time intervals where dilution rates were held constant are denoted on the figure. The simulated volume ratio of the N−1 perfusion bioreactor to CSTR is also denoted on the figure.

Once the cell bleed from the N-1 perfusion reactors was directed into the production bioreactors (CSTR's), the cell density of those reactors very quickly increased to above $20 \times 10^6$ viable cells/mL (FIG. 14). The flowrate of concentrated feeds added directly to the production bioreactors was increased as necessary as the cell density increased in order to maintain sufficient nutrients for continued cell growth and protein production. The nutrients were monitored by amino acid analysis (HPLC) and other metabolites (lactate, glucose, ammonia, osmotic strength, etc.) were monitored by means of NovaFlex Analyzers (Nova Biomedical, Waltham, MA). The feeding rates were adjusted so that the sum of the residual amino acids (not including alanine, as alanine is often at high levels in culture as a metabolic byproduct) was maintained above 30 millimolar and that any particular amino acid was not less than 0.2 millimolar. The feed consisted of a concentrated solution of glucose (50 grams/L), amino acids (600 millimolar), shear protectant (polyvinyl alcohol at 5.12 grams/L), vitamins and trace elements (some detailed in table 6).

TABLE 6

Media and feeds composition details

| Medium | Total Amino Acids (mM) | Glucose (g/L) | Sodium-L-Lactate (g/L) | Osmotic Strength (mOsm) |
|---|---|---|---|---|
| Basal medium for N-1 perfusion and CSTR production bioreactors | 120 | 4 | 0 | 280 |
| Perfusion medium (days 1-43) | 60 | 4.2 | 2.1 | 319 |
| Concentrated feed medium for production (CSTR) bioreactors | 607 | 50 | 0 | ~1100 |
| Saline diluent solution used for achieving high dilution rate in production bioreactors from days 10 to 26 (20 mM KCl, balance NaCl) | 0 | 0 | 0 | 250 |
| Concentrated glucose solution used for production bioreactors | 0 | 500 | 0 | 2777 |

The dipeptide glycine-tyrosine was also used in the concentrated feed to reduce complications of tyrosine solubility. For every 100 mL of concentrated feed medium added to the production bioreactor 2.5 mL of a 400 millimolar acidic stock solution of cystine was also added.

Since the goal of the experiment was to explore different dilution rates in the production bioreactor, it was realized that a saline diluent solution is also necessary to be fed to the production bioreactors, particularly when high dilution rates were being explored. This saline diluent consisted of water with 20 millimolar potassium chloride and the balance sodium chloride with a final osmotic strength of 250 mOsm/kg. Thus, in an embodiment, the production bioreactor is fed with a saline solution to help adjust the dilution rate and also to control the osmotic strength of the CSTR production bioreactor. In another embodiment, the CSTR production bioreactor is fed with a saline solution in an amount sufficient for the medium in the production bioreactor to achieve a final osmotic strength that is optimal for an increased productivity of the cells. In another embodiment, the CSTR production bioreactor is fed with a saline solution in an amount sufficient for the medium in the production bioreactor to achieve a final osmotic strength of about 100 to about 500 mOsm/kg, or to achieve a final osmotic strength of about 150 to about 400 mOsm/kg, or to achieve a final osmotic strength of about 150 to about 350 mOsm/kg, or any specific value therebetween. In another embodiment, the saline solution added to the production bioreactor is sufficient to produce a final osmotic strength of about 250 mOsm/kg.

Initially the levels of lactate in the production bioreactors increased very quickly (days 8-10, FIG. 11). For this reason, once the glucose was exhausted in the production bioreactors (day 10, FIG. 10) the feeding of glucose to the production bioreactors was limited. The glucose level was controlled by using a continuous feed of concentrated nutrients and glucose that was at a level of glucose that was predicted to be below that needed to balance the amount of amino acids contained in the feed (details in table 6 and as previously described). An additional feed of concentrated 500 gram/L glucose was fed directly and slowly to the two production bioreactors by means of pumps that were activated when pH reached the high-end set-point of 7.125. This method of control of lactate, High-end pH-Controlled Delivery of Glucose (HIPDOG) is described in detail in Gagnon et. al. 2011, Biotechnol Bioeng 108:1328-37. The HIPDOG control was used until day 26 in the production bioreactor using cell bleed from the target $40 \times 10^6$ N-1 perfusion bioreactor, and until day 22 in the production bioreactor using cell bleed from the target $80 \times 10^6$ N-1 perfusion bioreactor. After these time-points, day 22 and day 26, the residual glucose levels in the production bioreactors were maintained in what is believed to be a non-limiting range, generally above 0.3 grams/L, but more often in the 1-3 gram/L range (FIG. 10) for the remainder of the experiments by continuous feeding of the concentrated glucose solution (500 gram/L).

FIG. 14 shows the viable cell densities in the production bioreactors. The cell densities quickly increased initially, but then began to stabilize by day 10 to 14. The volume and concentration of cells entering the production bioreactors from the N-1 perfusion reactors were held constant from about day 10 until about day 32. At that point the volume of cells entering the production bioreactors was cut in half in order to simulate a larger bioreactor volume ratio difference of 1:10 (N-1 compared to production bioreactor volume). The ratio was changed again on about day 43 to simulate a ratio of 1:20. The timing of these changes are indicated with text on the graph of cell density in the production (CSTR) bioreactors (FIG. 7).

Figure 16:
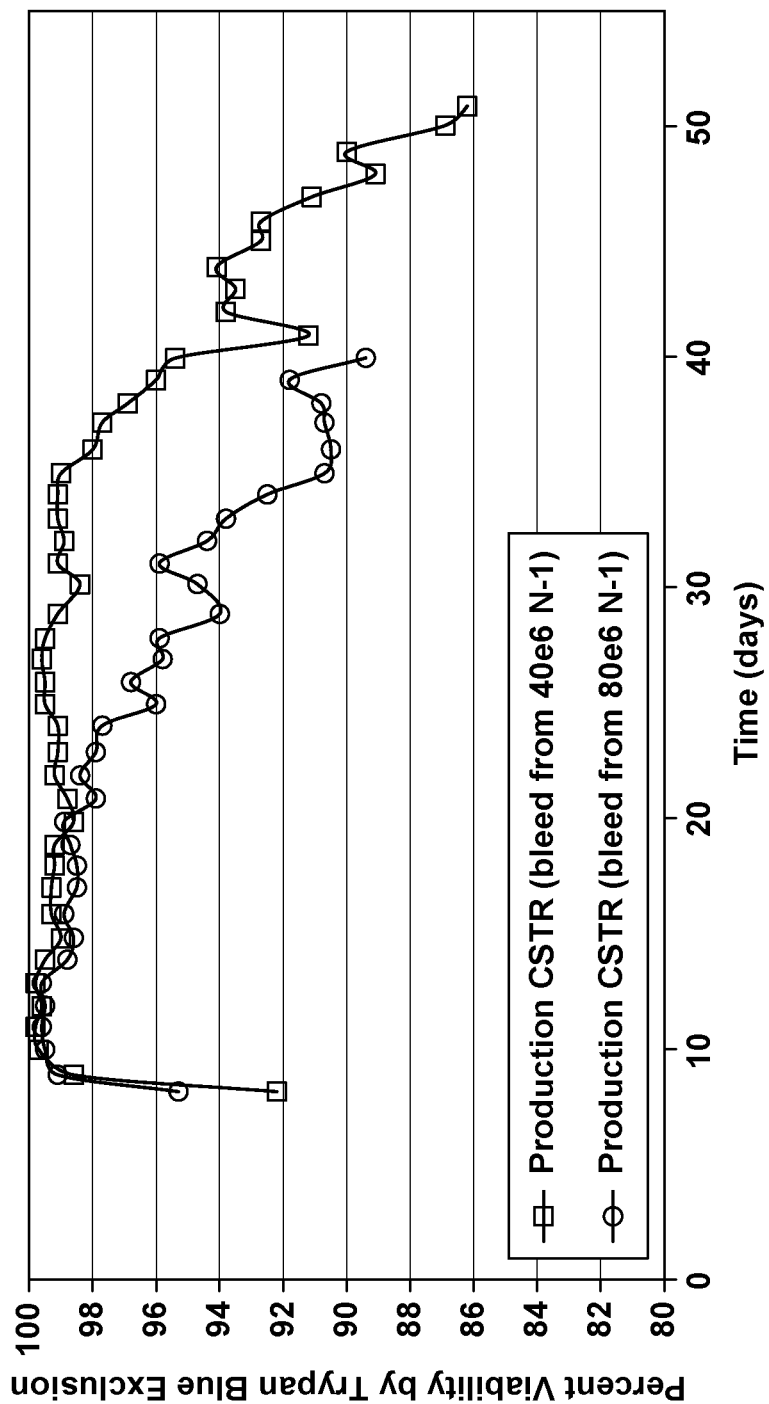
FIG. 16 is a plot showing the cell viabilities as measured by trypan blue dye exclusion as a function of time in the production bioreactors operating as continuous-flow stirred-tank reactors (CSTR's).
Figure 17:
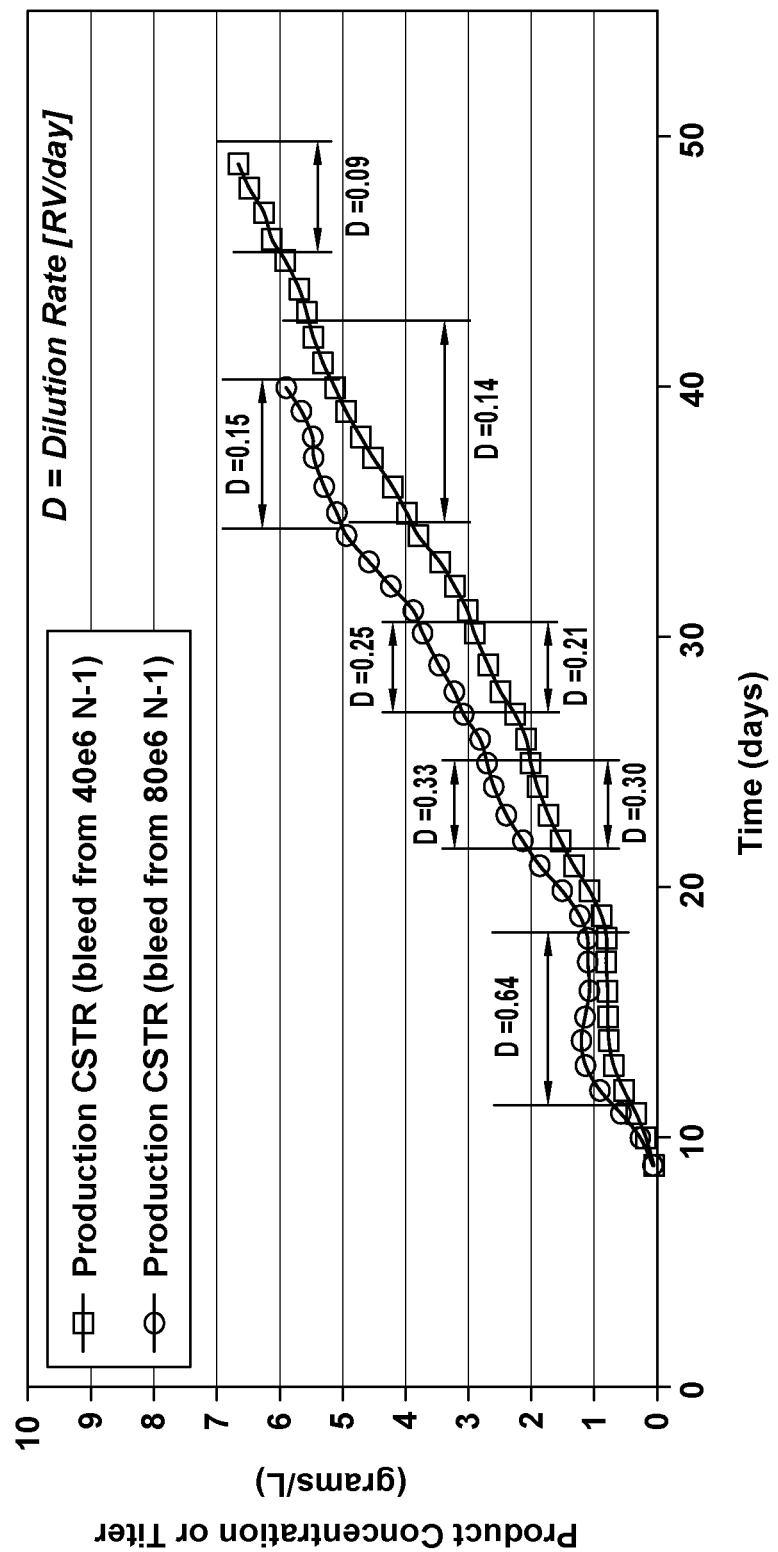
FIG. 17 is a plot showing the product concentration or titer as a function of time for the production bioreactors operating as continuous-flow stirred-tank reactors (CSTR's). Time intervals where dilution rates were held constant are denoted on the figure.

From day 13 to day 18 the volume of nutrient feeds to both of the production bioreactors were held roughly constant. The dilution rate (measured in reactor volumes per day, or reciprocal time) of the production bioreactor (shown in FIG. 15 and also in text on FIGS. 14 and 17) is the sum of the volumes of cell bleed, concentrated nutrient feed and saline diluent, concentrated glucose feed, and any minor additions of anti-foam and base titrant to control pH on the low end, divided by the reactor volume. The dilution rate was held relatively constant at an average value of 0.64 reactor volumes per day (FIG. 15) from days 13-18 for both production bioreactors. During this time period when the dilution rate on the two production bioreactors was held roughly constant, the cell density (FIG. 14), cell viability (FIG. 16), titer or product concentration (FIG. 17), and most other metabolites reached nearly constant values indicating that a steady-state condition had been achieved.

After day 18 the dilution rates of the production bioreactors were slowly reduced over the course of several days to 0.30 reactor volumes per day for the culture receiving cell bleed from the target $40 \times 10^6$ viable cell/mL N-1 perfusion reactor, and 0.33 reactor volumes per day for the culture receiving cell bleed from the target $80 \times 10^6$ viable cell/mL N-1 perfusion reactor. The reduction in dilution rates was accomplished by slowly decreasing the volume ratio of saline diluent to concentrated feed that was being added directly to the production bioreactors. As before, the cultures were monitored for nutrient levels and the concentrated nutrient feed rate was adjusted as necessary to feed sufficient nutrients for the changing cell densities.

By day 21 both production bioreactors had reached the next targeted dilution rate (0.30 and 0.33 reactor volumes/day). The production bioreactors were held at the target dilution rates for another 5 days until most culture parameters had reached nearly constant values. Due to the lower dilution rates that were being tested at this point, and for the rest of the experiment, it was impractical to wait until the cultures had reached completely unchanging values for every parameter.

From day 26 to 28 the dilution rates of the production bioreactors were again decreased by decreasing the volume ratio of saline diluent to concentrated feed that was being added directly to the production bioreactors. To achieve the reduced dilution rates that were held constant from days 28-31 (0.21 and 0.25 reactor volumes/day as shown in the figures, e.g., 15) it was necessary to completely eliminate the use of the saline diluent. From day 28 forward the feeds to the production bioreactors consisted only of the cell bleed from the associated N-1 perfusion reactor, the concentrated nutrient feed, a concentrated glucose feed, and trace amounts of antifoam. Negligible amounts of base titrant were required for the remainder of the experiment since the cells had shifted into a metabolic state in which no net lactic acid was being produced. Again the majority of metabolic parameters stabilized to near constant values by day 31.

On day 31 the volume of cell bleeds from the N-1 perfusion bioreactors being added to their associated production bioreactor (CSTR) were reduced by one half in order to simulate a production bioreactor with a volume ten times that of the N-1 reactor. To restate this, the volume of cell bleed being removed from the N-1 perfusion bioreactor was not changed, but a larger fraction of that cell bleed was now sent to waste rather than being added to the associated production bioreactor. This change in simulated volume ratio was necessary to attempt to study a dilution rate of the production bioreactor lower than that already tested without limiting the availability of nutrients to the culture. After the change in simulated volumes, the viable cell density of the production bioreactor receiving cell bleed from the target $80 \times 10^6$ cell/mL N-1 perfusion bioreactor decreased to just over $50 \times 10^6$ cells/mL. As this occurred, the requirement for concentrated nutrient feed slightly decreased until the effective dilution rate of the culture reached a value of approximately 0.15 reactor volumes/day on day 34. This dilution rate was held constant until day 41 at which time the experiment was completed for the production bioreactor receiving cell bleed from the target $80 \times 10^6$ cell/mL N-1 perfusion bioreactor. In a similar manner the effective dilution rate of the production bioreactor receiving cell bleed from the target $40 \times 10^6$ cell/mL N-1 perfusion bioreactor decreased to about 0.14 reactor volumes/day on day 34 and was held there until day 43 when the majority of parameters reached steady-state values.

Figure 15:
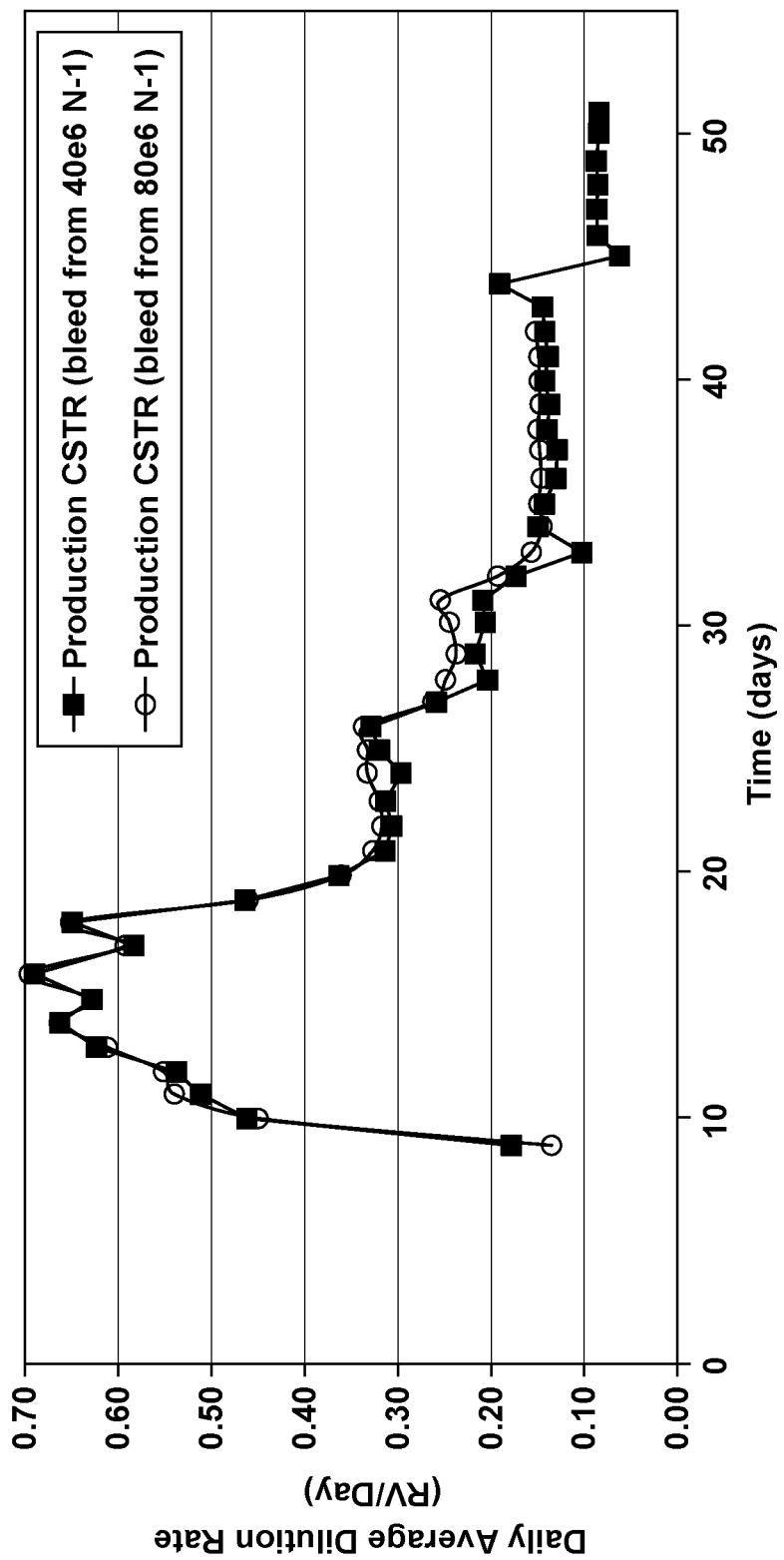
FIG. 15 is a plot showing the dilution rate of each of the production bioreactors operating as continuous-flow stirred-tank reactors (CSTR's) as a function of time.
Figure 18:
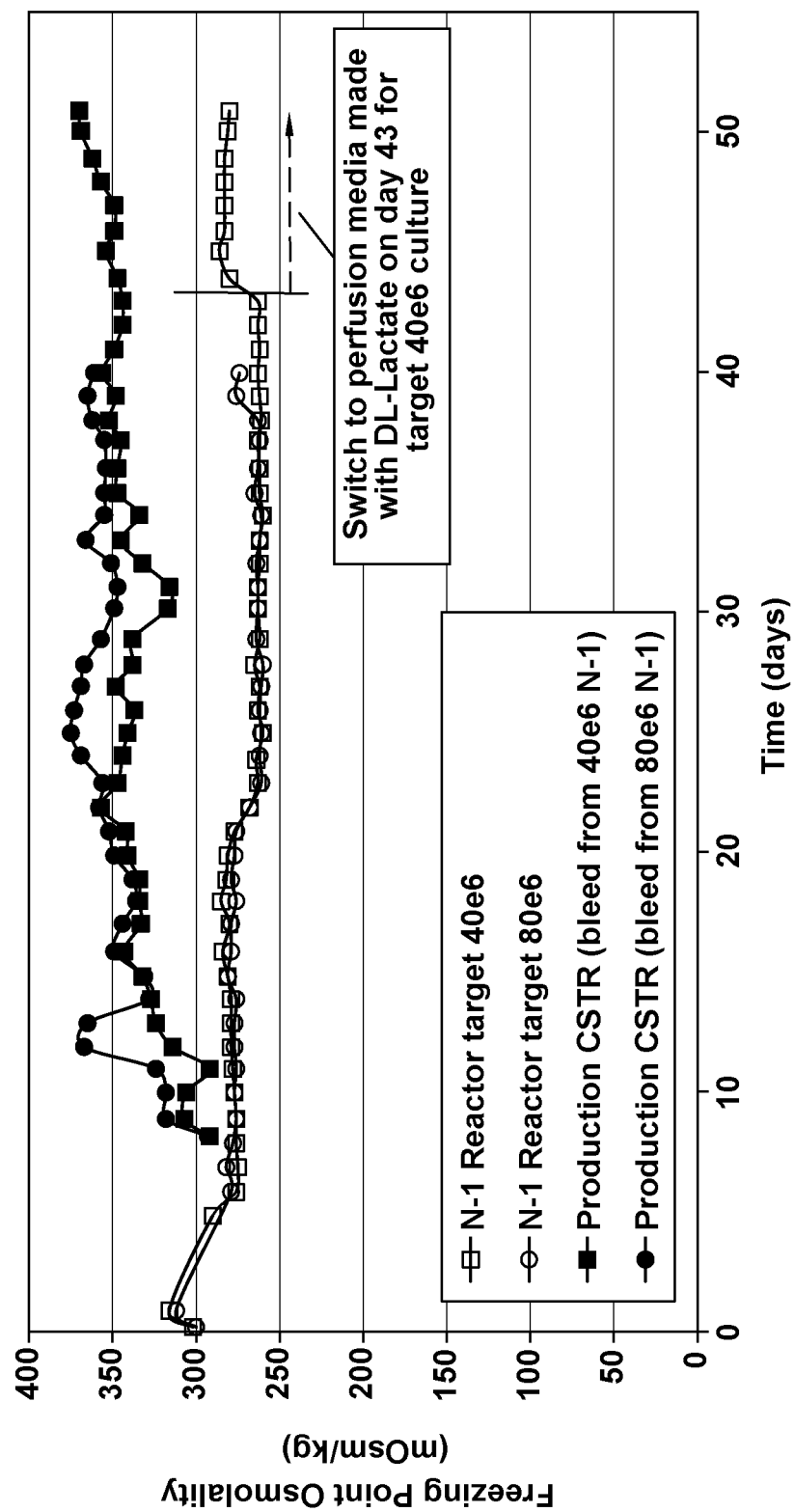
FIG. 18 is a plot showing the osmolality as a function of time for the N−1 continuous perfusion bioreactors (open symbols) and for the production bioreactors operating as CSTR's (solid symbols). Denoted on the figure is the time-point at which the perfusion medium was changed to contain the DL form of sodium lactate.

On day 43 the simulated volume ratio of N-1 perfusion bioreactor to production bioreactor was changed again, this time to 1:20. This allowed for the exploration of a dilution rate of 0.09 reactor volumes/day from days 46 to 50 for the production bioreactor receiving cell bleed from the target $40 \times 10^6$ cell/mL N-1 perfusion bioreactor (FIG. 15). Also on day 43, the formulation of perfusion medium being added to the target $40 \times 10^6$ cell/mL N-1 perfusion bioreactor was slightly altered. The L-sodium lactate level in the perfusion medium prior to day 43 had been 2.1 grams/L. On day 43 a switch was made to use a perfusion medium containing sodium DL-lactate, a more commercially available and economical alternative to the pure L-sodium lactate chemical. An assumption was made that the sodium DL-lactate concentrated solution obtained contained an equal ratio of D and L-isomers of lactate and that the cells in culture would likely only take up the L-isomer form. The sodium DL-lactate was added to a level of 4.2 grams/L such that the molar concentration of L-lactate in the perfusion medium would still be approximately 18.8 millimolar. An attempt was made to prepare the perfusion medium before and after the change to DL-lactate with the same osmotic strength. This was accomplished by compensating for the additional osmotic contribution of the added sodium D-lactate by reducing the amount of sodium chloride added to the perfusion medium. As a final step prior to sterile filtration during the medium preparation process, the osmotic strength is measured by a freezing point osmometer. Sodium chloride is normally added to the medium preparation to adjust the osmolality of the solution close to the desired value, in this case approximately 319 mOsm/kg. Despite the attempt to match the osmotic strength of the perfusion media there was a slight increase in the steady-state osmotic strength of the N-1 bioreactor around day 43 soon after the switch to the perfusion medium containing the DL-lactate (FIG. 18).

In separate flask tests of a pure form of sodium-D-lactate it was determined that within the normal ranges of use (0-5 grams/L) the D-lactate form does not register with the analytical equipment using the standard analysis methods. For this reason it is not surprising that after the change to the perfusion medium containing the DL-lactate (day 43) the level of lactate as measured in the target $40 \times 10^6$ cell/mL N-1 perfusion bioreactor did not change appreciably (FIG. 11).

Figure 19:
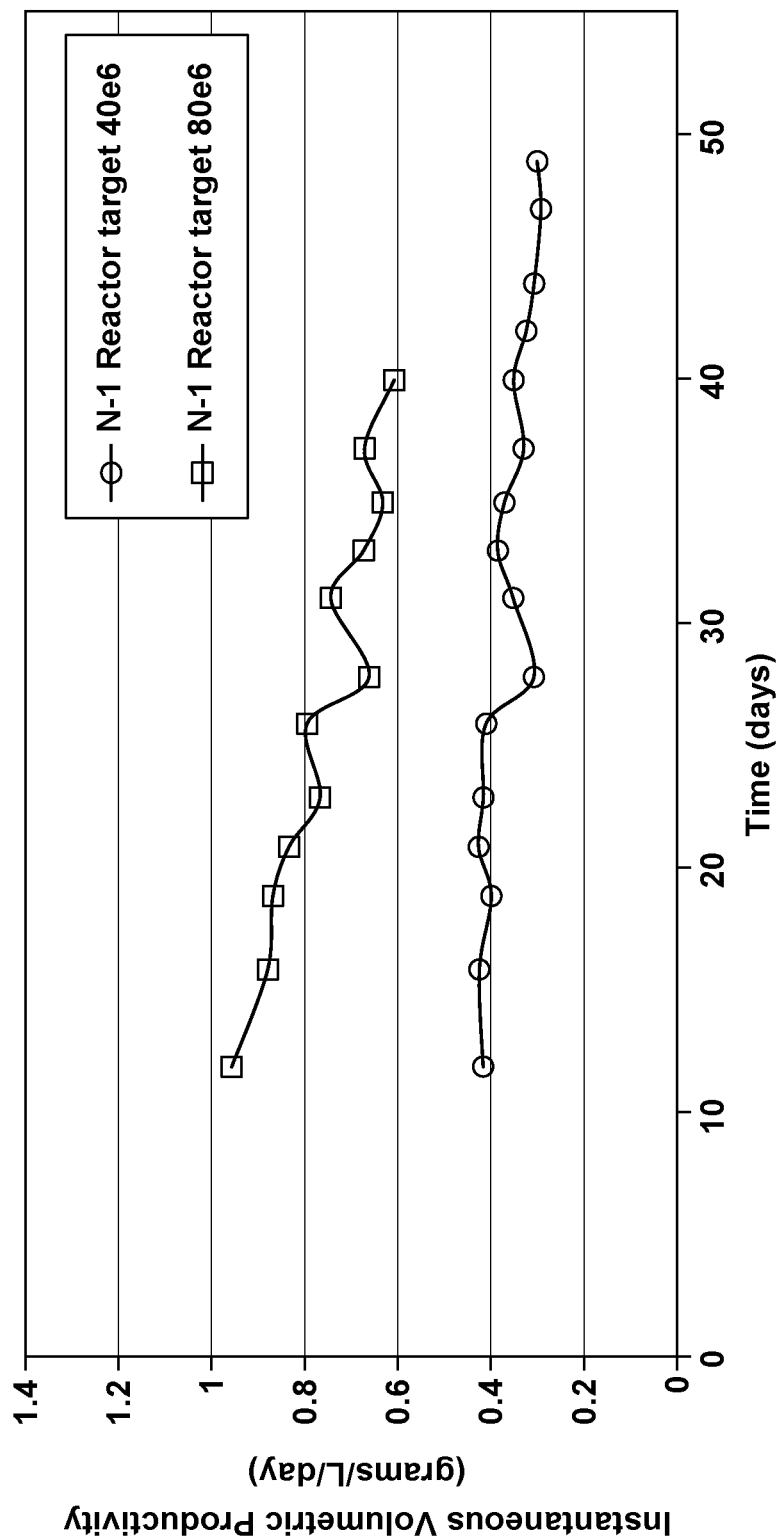
FIG. 19 is a plot showing the instantaneous volumetric productivity of the N−1 continuous perfusion bioreactors as considering operating independently. Calculated values assume that product is recovered from both the cell bleed the cell-free permeate leaving the cell retention system.
Figure 20:
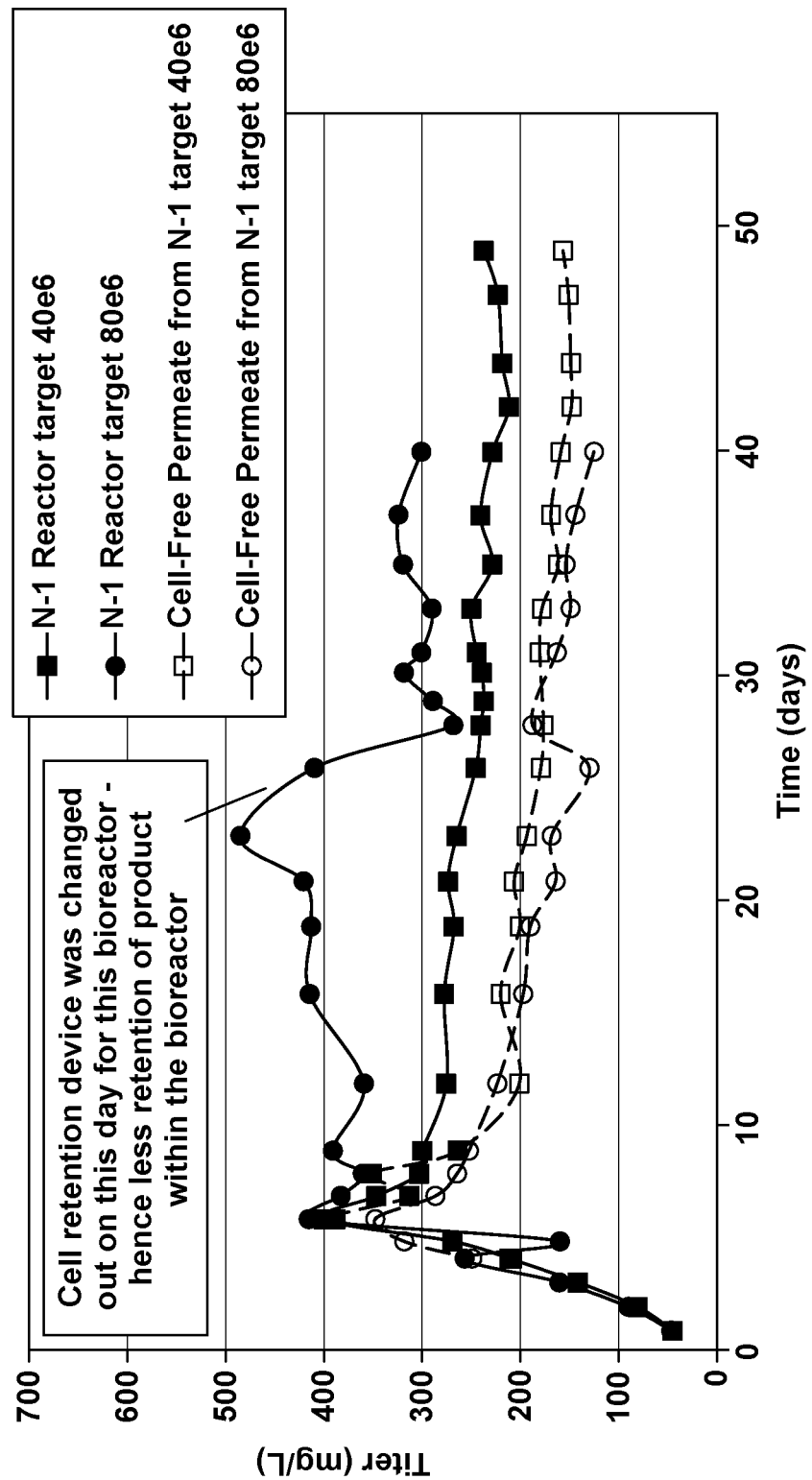
FIG. 20 is a plot showing the concentration of product (antibody) in the N−1 perfusion reactors and in the cell-free permeate leaving the cell retention devices.

The volumetric productivity of the N-1 perfusion bioreactors operating independently as perfusion bioreactors are shown in FIG. 19. This figure assumes that the perfusion bioreactor is operating as a production bioreactor and that the protein product is recovered from all streams leaving the bioreactor (the cell bleed and the cell-free permeate leaving the cell retention system). The volumetric productivity also considers minor changes in product concentration in the bioreactor that occurred when a small amount of selective concentration of product in the bioreactor occurred. This was mostly only evident in the N-1 perfusion bioreactor with the target $80 \times 10^6$ cell/mL density (FIG. 20, days 15-25).

Even though the operating conditions of the perfusion bioreactors are not changed significantly after about day 10, and the cell density, cell viability, and other culture parameters are nearly unchanged from day 10 to the end of the experiment for both perfusion bioreactors, the volumetric productivity slowly declines by about 29% for the target $40 \times 10^6$ cell/mL N-1 perfusion bioreactor (from day 12 to 48) and about 36% for the target $80 \times 10^6$ cell/mL N-1 perfusion bioreactor (from day 12 to 40). This loss in productivity is likely a result of moderate genetic instability of the producer CHO cell line B.

Figure 21:
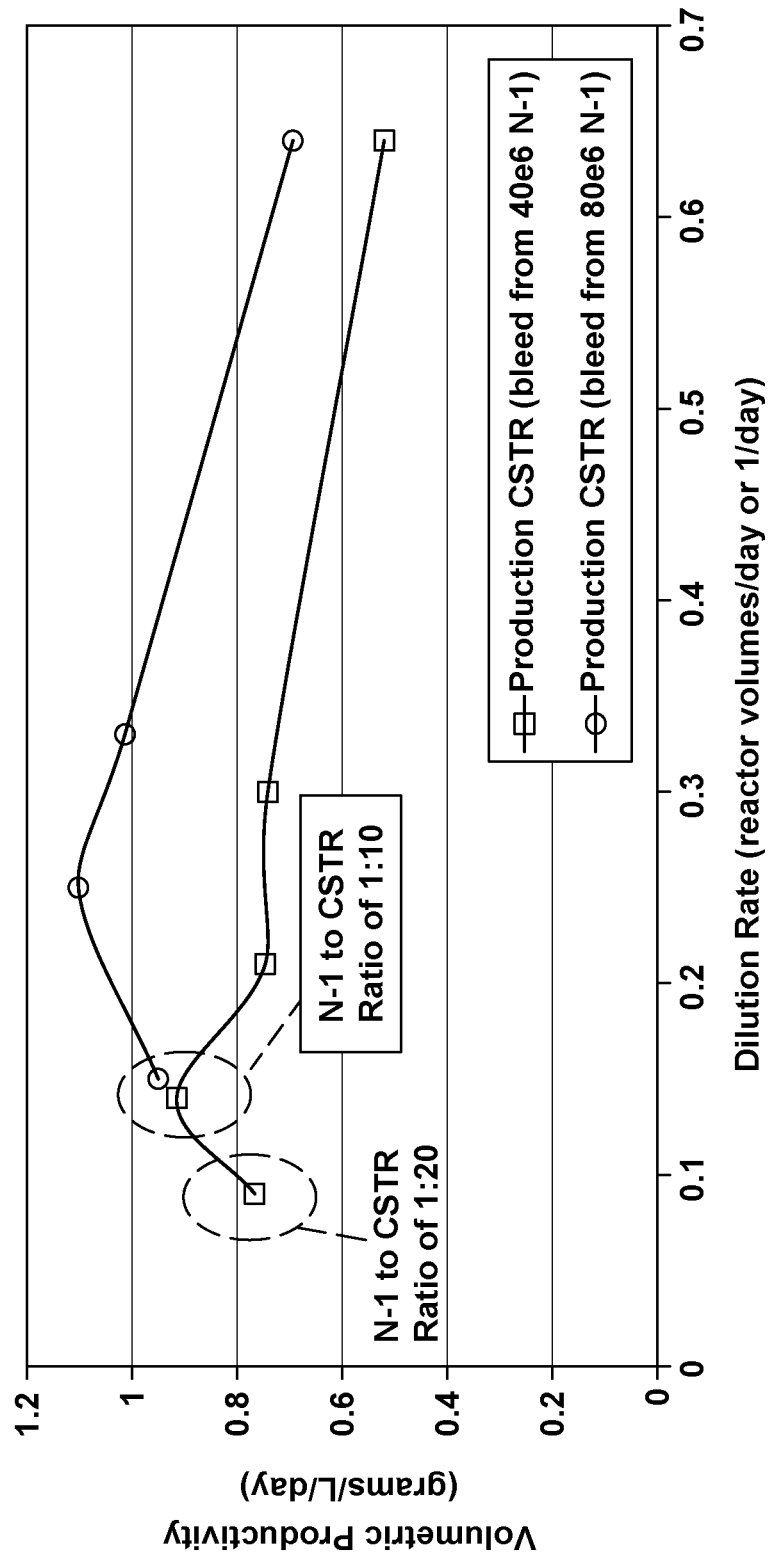
FIG. 21 is a plot showing the steady-state volumetric productivity of the linked N−1 continuous perfusion bioreactor to CSTR system, graphed as a function of production CSTR dilution rate. The volume ratio of N−1 continuous perfusion bioreactor to production CSTR is denoted for several conditions. All points not specifically denoted used the 1:5 volume ratio.

The steady-state volumetric productivity of the combined N-1 perfusion linked to production bioreactor (CSTR) system is shown in FIG. 21. The volumetric productivity is graphed relative to the dilution rates used in the production bioreactors. The steady-state volumetric productivities of the linked N-1 perfusion and CSTR production bioreactor were calculated in the following manner. A material balance was performed to determine the rate of production of product protein in the production bioreactor. The material balance considered the product concentration and volume of liquid entering the production bioreactor from the N-1 bioreactor, the rate of product concentration increase in the production bioreactor, and the product concentration at any time-point in the production bioreactor and its rate of removal (the dilution rate). This calculation yielded the total mass of product produced in the CSTR which was then plotted against time. A linear regression was then used to more accurately determine the production of mass per time per reactor volume value, only considering time points when the dilution rate was held constant and the cell density had reached a relatively constant value. This estimation was then added to the production rate of the N-1 bioreactor (again assuming the correct simulated volume ratio of N-1 to production bioreactor, and only considering the volume of fluid that enters the production bioreactor) for the final volumetric productivity estimation of the linked N-1 perfusion bioreactor to production CSTR system for any particular dilution rate.

Multiplying the product concentration in the CSTR production bioreactor at the last time-point for any particular steady-state by the dilution rate (in reciprocal time) will also yield an estimate of the overall volumetric productivity of the linked bioreactor system. However, unless the product concentration is unchanging at the time-point used, this calculation will give a slight underestimate of the actual steady-state volumetric productivity of the system.

As can be seen in FIG. 21, for many of the steady-state conditions, the volumetric productivity of the combined N-1 perfusion and production bioreactor is considerably higher than the volumetric productivities of the N-1 perfusion bioreactors operating independently. The one exception to this generalization might be the volumetric productivity of the target $80 \times 10^6$ cell/mL N-1 perfusion bioreactor at the earliest time-points on FIG. 19. This perfusion bioreactor was operating at a perfusion rate of 3.6 reactor volumes/day and a very high cell density. The practical operation of such a bioreactor at very large scale might entail significant challenges due to the volumes of medium that would be required to be prepared and stored, and also the difficulty of designing a cell retention system that could function at very large volumes. Additionally, since delivering sufficient oxygen and removing sufficient carbon dioxide becomes more problematic at large scale, the very high viable cell densities ($80 \times 10^6$ cells/mL) might pose substantial engineering complications.

The linked N-1 perfusion to CSTR production bioreactor alleviates many of these issues by dramatically reducing the size of the perfusion bioreactor and drastically reducing the overall volumes of medium required. The linked bioreactor system maintains volumetric productivities approximately the same as a continuous perfusion bioreactor operating at high density and at the high perfusion rates necessary to maintain that high cell density. FIG. 21 shows that the optimal dilution rate for operating the CSTR production bioreactor occurs over a quite broad range from around 0.1 to approximately 0.35 reactor volumes per day. Due to the slow loss in productivity of the cell line as indicated in FIG. 19, and the fact that the high dilution rate conditions were investigated first during the experiment, it is likely that the steady-state volumetric productivities as presented in FIG. 21 for the low dilution rates might be slight underestimates of the actual productivity achievable.

Table 7 lists some additional details that relate to the highest volumetric productivity conditions for the two linked N-1 perfusion to CSTR systems as indicated on FIG. 21.

TABLE 7

Various process parameters relating to the two highest steady-state volumetric productivities for the linked N-1 perfusion and CSTR production bioreactor system. A comparison of the perfusion bioreactors operating independently as production bioreactors and as part of the linked bioreactor system.

| Process | Perfusion rate (reactor volumes/day) | Dilution Rate of CSTR (reactor volumes/day) or 1/day) | Total Medium Consumption Rate of Linked Bioreactor System (production bioreactor volumes/day) | Grams of protein product produced per liter of medium and nutrient feed consumed (grams/L) | Maximum Volumetric Productivity (grams/L production bioreactor volume/day) |
|---|---|---|---|---|---|
| Sustainable Perfusion with target $40 \times 10^6$ cells/mL (perfusion reactor operating independently) | 1.76 | NA | NA | 0.24 | 0.42 |
| Linked N-1 Perfusion to CSTR N-1 1/10th volume of CSTR (using bleed from target $40 \times 10^6$ cells/mL perfusion reactor) | NA | 0.14 | 0.24 | 3.83 | 0.92 |
| Sustainable Perfusion with target $80 \times 10^6$ cells/mL (perfusion reactor operating independently) | 3.60 | NA | NA | 0.27 | 0.96 |
| Linked N-1 Perfusion to CSTR N-1 1/5th volume of CSTR (using bleed from target $80 \times 10^6$ cells/mL perfusion reactor) | NA | 0.25 | 0.82 | 1.34 | 1.10 |

The efficiency of medium or feed use is significantly higher in the linked bioreactor systems when compared with the perfusion bioreactors operating independently. The condition with the highest efficiency of medium usage, 3.83 grams product protein produced per liter of medium or feed used in the system as a whole for the linked system, is quite high, even when compared with a mammalian cell culture bioreactor operating in a fed-batch mode.

While in the current experiment the cell bleed rate was adjusted manually each day to ensure that the two N-1 perfusion cultures maintained a cell density close to their target values, in an industrial setting with a well understood process, the cell density is monitored with any number of sterilizable probes that utilize capacitance measurements (or other technologies) to estimate the viable cell mass in an operating bioreactor. A computer control algorithm could then be written to continuously vary the amount of cell bleed removed from the N-1 perfusion bioreactor. Presumably in a linked N-1 perfusion to CSTR production bioreactor system all cell bleed would be immediately transferred to the production bioreactor.

Since the effective dilution rate of the CSTR production bioreactor is dependent to a large degree on the volume of liquid entering the vessel from the continuous N-1 perfusion bioreactor, in an embodiment, the cell bleed from the N-1 perfusion bioreactor is further concentrated (by removing additional liquid from the cell bleed) before it is transferred into the CSTR production bioreactor. This concentration of the cell bleed is particularly valuable when the N-1 perfusion bioreactor is operating at a low cell density and/or when it is determined in experiments that low dilution rates in the CSTR production bioreactor yielded higher volumetric productivities for the system as a whole. The further concentration of the cell bleed (if necessary) is performed by any practical cell retention method (continuous micro-filtration, acoustic wave settling, hydrocylone, etc.).

Since the cell bleed from the N-1 perfusion reactors brings a considerable fraction of the total volume of fluid into the production reactor (depending upon the conditions), in an embodiment, to minimize the addition of feed medium to the production bioreactor, a very high nutrient content medium is used to perfuse the N-1 bioreactor. Since the cells in the N-1 perfusion reactor would not be able to consume all of the nutrients from the perfusion medium, significant amounts of nutrients would then flow in the production bioreactor. There is a limit to this capability however in that the growth rate of cells in the presence of very high levels of some amino acids may be considerably limited. Additionally, since most of the perfusion medium entering the N-1 bioreactor is lost to waste in the cell free permeate, the additional costs of discarding large volumes of high nutrient content perfusion medium would have to be considered.

In a similar manner to the reasoning for potentially concentrating the cell bleed before transfer, having a nutrient feed directly to the CSTR production bioreactor that is highly concentrated is important for the linked system to function effectively and achieve high volumetric productivities. A very dilute feed medium might dilute the biomass in the CSTR production bioreactor by increasing the effective dilution rate of the bioreactor. With mammalian cells that typically have maximum doubling times near or above one day, any effective dilution rate near or above 1.0 reactor volumes/day (or 1/day) might result in a very low cell density in the CSTR production bioreactor and therefore low productivity in the linked bioreactor system.

In the example we have described above, during conditions in which dilution rates were above 0.20 reactor volumes/day (1/day) a saline diluent as described in table 3 was used to dilute the concentrated feeds to the CSTR production bioreactor. FIG. 21 shows that reasonable volumetric productivities can be achieved with the linked bioreactor system at dilution rates even as high as 0.64 reactor volumes per day. High dilution rates dilute the viable cell mass in the CSTR and tend to drive productivity lower, but high dilution rates also simultaneously flush cell-generated inhibitory compounds out of the bioreactor system and therefore increase the growth rate of cells. These competing factors partially balance each other out which allows for the cell density at high dilution rates to still be maintained reasonably high, and as a result reasonably high volumetric productivities can still be achieved. Thus, in one embodiment, the dilution rate of the production bioreactor is from about 0.1 volumes/day to about 1.25 volumes/day. In another embodiment, the dilution rate of the production bioreactor of the subject technology is from about 0.2 volumes/day to about 1.0 volumes/day; or from about 0.2 to about 0.75 volumes/day; or about 0.2 volumes/day or about 0.65 volumes/day. In another embodiment, the dilution rate of the production bioreactor of the subject technology is about 0.1 volumes/day; or is about 0.2 volumes/day; or is about 0.25 volumes/day; or is about 0.3 volumes/day; or is about 0.35 volumes/day; or is about 0.4 volumes/day; or is about 0.45 volumes/day; or is about 0.5 volumes/day; or is about 0.6 volumes/day; or is about 0.7 volumes/day; or is about 0.8 volumes/day; or is about 1.0 volumes/day; or is about 1.25 volumes/day.

At 0.64 reactor volumes per day the average residence time of product being generated in the bioreactor is approximately 1.56 days. This residence time is far less than the average residence time of product made in a fed-batch bioreactor. For this reason, the linked N-1 perfusion to CSTR production bioreactor system might have significant advantages over the fed-batch mode of bioreactor operations in the case of labile proteins. Additionally, through use of increased volumes of the saline diluent added to the production bioreactor the dilution rate of the linked bioreactor system could be manipulated to reduce the residence time of product protein without overly reducing the volumetric productivity of the system as a whole. The same result of course could be achieved by simply manipulating the concentration of the feed media that flows directly in to the production bioreactor. Thus, in an embodiment, the product residence time in the production bioreactor of the subject technology is from about 1 day to about 10 days. In another embodiment, the product residence time in the production bioreactor of the subject technology is about 1 day, or about 2.0 days; or about 2.5 days; or about 3.0 days; or about 3.5 days; or about 4 days, or about 5 days, or about 6 days, or about 7 days, or about 8 days, or about 9 days, or about 10 days. In another embodiment, the residence time of the cells in the production bioreactor of the subject technology is less than about 10 days.

As mentioned earlier in this text, the strategy of limiting glucose availability in the CSTR production bioreactors was used at the beginning of the experiment (HIPDOG technology). This limited the accumulation of lactate in the bioreactors. Since the low dilution rates for the CSTR's proved to be the most productive, in an industrial application it might be of value to immediately or very quickly move to a condition of low dilution rates. Presumably when the first cells flow into the production bioreactor CSTR from the N-1 perfusion bioreactor the CSTR bioreactor will be a least partially full of fresh basal medium. In a highly proliferative state in the presence of freely available glucose those cells might start to produce large amounts of lactic acid, and with pH control this would also mean a high osmotic strength as the lactic acid was neutralized. Any lactate accumulated (and its associated high osmotic strength) in the CSTR early in the culture while the bioreactor is filling or produced immediately thereafter while at very low dilution rates would be very slow to be diluted out of the culture system. For this reason there is significant value in utilizing a glucose limiting technology such as high-end pH-controlled delivery of glucose (HIPDOG) in the initial startup phase of the CSTR production bioreactor. Without some method of control of initial lactate production, high levels of lactate could accumulate in the production bioreactor such that after only several days of operation little or no growth would be achievable in the production bioreactor. When CHO cells in culture are exposed to a high lactate concentration sometimes a positive feed-back condition occurs in which lactate production from glucose is significantly upregulated. Such a condition might significantly delay or even make unachievable the attainment of a steady-state condition with high volumetric productivity at low dilution rates. While the HIPDOG glucose limiting strategy worked well in the current experiment, a shift to a low pH control set-point or temperature lower than 36.5° C. might also or alternatively be used to minimize lactate formation in the CSTR production bioreactor for a period of time when it is first started. Both lower pH and lower temperature might slow growth and decrease cellular productivity, so the use of these setpoint control changes would have to be balanced against the need to control lactate formation. The optimal pH setpoint would likely be lower than 7.0 for this purpose, likely between 6.7 and 7.0. The optimal temperature would likely be between 30-35° C.

It will be apparent to those skilled in the art that various modifications and variations can be made to the described embodiments without departing from the spirit and scope of the claimed methods. Thus, it is intended that present claimed methods cover the modifications and variations of the embodiments described herein provided that they come within the scope of the appended claims and their equivalents.

INDUSTRIAL APPLICABILITY

The device and methods disclosed herein are useful for linked-perfusion-to-CSTR cell culture biomaufacturing, and thus for improving industrial methods for manufacturing recombinant and/or therapeutic proteins.

What is claimed is:

1. A linked culture system, comprising:
    a cell culture comprising a gene that encodes a protein of interest;
    a culture bioreactor (N–1 bioreactor) configured for culturing cells, wherein the culture bioreactor is a continuous perfusion culture bioreactor;
    a production bioreactor (N bioreactor), wherein the production bioreactor is a continuously stirred tank reactor (CSTR) fluidly connected to the culture bioreactor and designed to receive cells as inoculum from the culture bioreactor; and
    a pump configured to pump at least a portion of the cells as a cell bleed from the culture bioreactor to the production bioreactor in a continuous or semi-continuous mode;
    wherein the production bioreactor is configured to operate under conditions that allow production of the protein of interest.

2. The linked culture system according to claim 1, wherein the system is linked to a downstream purification system configured for harvesting the protein of interest from the production bioreactor.

3. The linked culture system according to claim 2, wherein the downstream processing system is configured for continuous harvesting of the protein of interest.

4. The linked culture system according to claim 1, wherein the production bioreactor has no cell retention device.

5. The linked culture system according to claim 1, wherein volume ratio of the culture bioreactor to the production bioreactor is about 1:1 to about 1:20.

6. The linked culture system according to claim 1, wherein the pump is configured to pump the cells in semi-continuous mode comprising the cell transfer once at every period of time from 2 minutes to 24 hours or at any interval therebetween.

7. The linked culture system according to claim 1, wherein the system includes a second culture bioreactor that is configured to operate in parallel with a first culture bioreactor and configured to alternate in producing inoculum for transfer to the production bioreactor.

8. The linked culture system according to claim 7, wherein the second culture bioreactor is a continuous perfusion culture bioreactor.

9. The linked culture system according to claim 1, wherein the cells are CHO cells, HEK-293 cells, VERO cells, NSO cells, PER.C6 cells, Sp2/0 cells, BHK cells, MDCK cells, MDBK cells or COS cells.

10. The linked culture system according to claim 9, wherein the cells are CHO cells.

11. The linked culture system according to claim 1, wherein the production bioreactor has a volumetric productivity of at least 0.6 grams per liter per day for a period of at least 14 days.

12. The linked culture system according to claim 1, wherein the production bioreactor has a product residence time of about 1 to about 10 days.

13. The linked culture system according to claim 1, wherein the production bioreactor has a dilution rate of about 1 to about 0.1 volume per day.

* * * * *